(12) United States Patent
Miwa et al.

(10) Patent No.: US 7,723,061 B2
(45) Date of Patent: May 25, 2010

(54) **METHOD FOR DIAGNOSING RENAL DISORDER, HEMOLYTIC UREMIC SYNDROME AND ENTEROHEMORRHAGIC INFECTIOUS DISEASE CAUSED BY *ESCHERICHIA COLI***

(75) Inventors: Kunio Miwa, Shizuoka (JP); Junko Sugatani, Shizuoka (JP)

(73) Assignee: Fuso Pharmaceutical Industries, Ltd., Osaka (JP)

( * ) Notice: Subject to any disclaimer, the term of this patent is extended or adjusted under 35 U.S.C. 154(b) by 0 days.

(21) Appl. No.: 12/043,067

(22) Filed: Mar. 5, 2008

(65) Prior Publication Data

US 2008/0274484 A1    Nov. 6, 2008

Related U.S. Application Data

(62) Division of application No. 10/110,582, filed as application No. PCT/JP00/06972 on Oct. 6, 2000, now Pat. No. 7,351,541.

(30) Foreign Application Priority Data

Oct. 13, 1999    (JP) ................. 11-291096

(51) Int. Cl.
*G01N 33/53* (2006.01)
*G01N 33/00* (2006.01)
*G01N 33/566* (2006.01)

(52) U.S. Cl. .................. 435/7.92; 435/7.1; 436/85; 436/501

(58) Field of Classification Search ............... None
See application file for complete search history.

(56) References Cited

U.S. PATENT DOCUMENTS 6,252,046 B1    6/2001   Okubo et al.

FOREIGN PATENT DOCUMENTS

JP    10-271996    10/1998
WO    WO-98/43997    10/1998

OTHER PUBLICATIONS

Ishikawa (Nephrol Dial Transplant 1998 13:1615-1616).*
Ishikawa et al., (Rinsho Byori, 1999 47(5): 402-7).*
Ishikawa, (Ann Med 2000, 32:90-93).*
Kanno et al., (NEJM Jun. 8, 1995 332(23):1540-1545).*
Taguchi et al., (Kidney Intl. 1998;53:161-8).*
Kwon et al., Seminars in Nephrology. May 2001 21(3):231-238.*
Frokiaer, et al., (Am J Med Sci Nov. 1998 316(5):291-299).*

(Continued)

*Primary Examiner*—Cherie M Woodward
(74) *Attorney, Agent, or Firm*—Marshall, Gerstein & Borun LLP

(57) ABSTRACT

Methods for diagnosing renal disorder, hemolytic uremic syndrome and enterohemorrhagic *E. coli* infectious disease at an early stage, and for diagnosing the severity of these diseases are provided. Detection of excretion of AQP2 and/or molecules derived therefrom into urine of a subject, or determination of the amount of excretion of the same is conducted to diagnose the morbidity or the severity of renal disorder, hemolytic uremic syndrome and enterohemorrhagic *E. coli* infectious disease of the subject. For the detection and determination of AQP2, an immunochemical process may be suitably employed in which an antibody that specifically recognizes AQP2.

9 Claims, 14 Drawing Sheets

OTHER PUBLICATIONS

Ausubel et al. (Eds.), Short Protocols in Molecular Biology. 4*th* Edition, John Wiley & Sons, Inc. 11-4-11-12 1999.

Elliot et al., Urinary excretion of aquaporin-2 in humans: A potential marker of collecting duct responsiveness to vasopressin. *J. Am. Soc. Nephrol.* 7: 403-9 (1996).

Frokiaer et al., *Am. J. Med. Sci.* 316: 291-9 (1998).

Ishikawa et al., *Rinsho Byori.* 47:402-7 (1999).

Ishikawa et al., Urinary excretion of aquaporin-2 in disorders of water metabolism. *Nephrol. Dial. Transplant.* 13: 1615-6 (1998).

Ishikawa et al., Urinary excretion of aquaporin-2 in disorders of water metabolism. *Jpn. J. Clin. Pathol.* 47: 402-7 (1999).

Ishikawa, Urinary excretion of aquaporin-2 in pathological states of water metabolism. *Ann. Med.* 32: 90-93 2000.

Kanno et al., Urinary excretion of aquaporin-2 in patients with diabetes insipidus, *New Engl. J. Med.* 332: 1540-5 1995.

Kim et al., Diminished adenylate cyclase activity and aquaporin 2 expression in acute renal failure rats. *Kidney Int.* 57: 1643-50 (2000).

Kwon et al., Physiology and pathophysiology of renal aquaporins. *Semin. Nephrol.* 21: 231-8 (2001).

Saito et al., Urinary excretion of aquaporin-2 in the diagnosis of central diabetes insipidus. *J. Clin. Endocrinol. Metabol.* 82: 1823-7 (1997).

Sei Sasaki, Aquaporin. *J. Clin. Exper. Med.* 173: 745-8 (1995).

Stedman's Medical Dictionary, 27*th* edition, Lippincott Williams & Wilkins (2000). "morbidity".

Sugatani et al., Urinary concentrating defect in rats given shiga toxin: Elevation in urinary AQP2 level associates with polyuria. *Life Sci.* 71: 171-89 (2002).

Taguchi et al., Verotoxins induce apoptosis in human renal tubular epithelium derived cells. *Kidney Int.* 53: 1681-8 (1998).

Umenishi et al., *Kidney Int.* 62: 228-93 (2002).

International Search Report, PCT/JP00/06972.

European Search Report, EP-00964707.4, dated Oct. 14, 2004.

Canadian Office Action, CA-2,386,895, dated Jun. 22, 2006.

Canadian Office Action, CA-2,386,895, dated May 28, 2004.

* cited by examiner

Fig. 2

SEQUENCE LISTING

<160> NUMBER OF SEQ ID NOS: 10

<210> SEQ ID NO 1
<211> LENGTH: 16
<212> TYPE: PRT
<213> ORGANISM: Homo Sapiens
<220> FEATURE:
<223> OTHER INFORMATION: Carboxy terminal Peptide of Human AQP2

<400> SEQUENCE: 1

Cys Val Glu Leu His Ser Pro Gln Ser Leu Pro Arg Gly Thr Lys Ala
 1               5                  10                  15

<210> SEQ ID NO 2
<211> LENGTH: 16
<212> TYPE: PRT
<213> ORGANISM: Homo Sapiens
<220> FEATURE:
<223> OTHER INFORMATION: Carboxy terminal Peptide of Human AQP1

<400> SEQUENCE: 2

Cys Leu Asp Ala Asp Asp Ile Asn Ser Arg Val Glu Met Lys Pro Lys
 1               5                  10                  15

<210> SEQ ID NO 3
<211> LENGTH: 17
<212> TYPE: PRT
<213> ORGANISM: Homo Sapiens
<220> FEATURE:
<223> OTHER INFORMATION: Carboxy terminal Peptide of Human AQP3

<400> SEQUENCE: 3

Cys Glu Glu Glu Asn Val Lys Leu Ala His Val Lys His Lys Glu Gln
 1               5                  10                  15

Ile

<210> SEQ ID NO 4
<211> LENGTH: 16
<212> TYPE: PRT
<213> ORGANISM: Homo Sapiens
<220> FEATURE:
<223> OTHER INFORMATION: Carboxy terminal Peptide of Human AQP4

<400> SEQUENCE: 4

Cys Glu Lys Lys Gly Lys Asp Gln Ser Gly Glu Val Leu Ser Ser Val
 1               5                  10                  15

<210> SEQ ID NO 5
<211> LENGTH: 23
<212> TYPE: PRT
<213> ORGANISM: Homo Sapiens
<220> FEATURE:
<223> OTHER INFORMATION: Carboxy terminal Peptide of Human AQP5

<400> SEQUENCE: 5

Cys Glu Pro Asp Glu Asp Trp Glu Glu Gln Arg Glu Glu Arg Lys Lys
 1               5                  10                  15

Thr Met Glu Leu Thr Thr Arg
            20

<210> SEQ ID NO 6
<211> LENGTH: 16
<212> TYPE: PRT
<213> ORGANISM: Rattus sp.

```
<220> FEATURE:
<223> OTHER INFORMATION: Carboxy terminal Peptide of Murine AQP1

<400> SEQUENCE: 6

Cys Leu Asp Ala Asp Asp Ile Asn Ser Arg Val Glu Met Lys Pro Lys
 1               5                  10                  15

<210> SEQ ID NO 7
<211> LENGTH: 16
<212> TYPE: PRT
<213> ORGANISM: Rattus sp.
<220> FEATURE:
<223> OTHER INFORMATION: Carboxy terminal Peptide of Murine AQP2

<400> SEQUENCE: 7

Cys Val Glu Leu His Ser Pro Gln Ser Leu Pro Arg Gly Ser Lys Ala
 1               5                  10                  15

<210> SEQ ID NO 8
<211> LENGTH: 16
<212> TYPE: PRT
<213> ORGANISM: Rattus sp.
<220> FEATURE:
<223> OTHER INFORMATION: Carboxy terminal Peptide of Murine AQP3

<400> SEQUENCE: 8

Cys Glu Ala Glu Asn Val Lys Leu Ala His Met Lys His Lys Glu Gln
 1               5                  10                  15

<210> SEQ ID NO 9
<211> LENGTH: 18
<212> TYPE: PRT
<213> ORGANISM: Rattus sp.
<220> FEATURE:
<223> OTHER INFORMATION: Carboxy terminal Peptide of Murine AQP4

<400> SEQUENCE: 9

Cys Ile Asp Ile Asp Arg Gly Asp Glu Lys Lys Gly Lys Asp Ser Ser
 1               5                  10                  15

Gly Glu

<210> SEQ ID NO 10
<211> LENGTH: 23
<212> TYPE: PRT
<213> ORGANISM: Rattus sp.
<220> FEATURE:
<223> OTHER INFORMATION: Carboxy terminal Peptide of Murine AQP5

<400> SEQUENCE: 10

Cys Glu Pro Glu Glu Asp Trp Glu Asp His Arg Glu Glu Arg Lys Lys
 1               5                  10                  15

Thr Ile Glu Leu Thr Ala His
                 20
```

METHOD FOR DIAGNOSING RENAL DISORDER, HEMOLYTIC UREMIC SYNDROME AND ENTEROHEMORRHAGIC INFECTIOUS DISEASE CAUSED BY *ESCHERICHIA COLI*

This application is a divisional of U.S. patent application Ser. No. 10/110,582, filed Jul. 23, 2002, incorporated herein by reference in its entirety, which is the U.S. national stage of International Application No. PCT/JP00/06972, filed Oct. 6, 2000, incorporated herein by reference in its entirety, which claims priority benefit of Japanese Patent Application No. 11-291096, filed Oct. 13, 1999.

FIELD OF THE INVENTION

The present invention relates to methods for diagnosing renal disorder, hemolytic uremic syndrome or enterohemorrhagic infectious diseases by *Escherichia coli*, and for diagnosing the severity of these diseases by detecting the excretion of aquaporin 2 (hereinafter referred to as "AQP2") and/or derived molecules therefrom into urine of a subject, or by determining the excreted amount of aquaporin 2 and/or derived molecules therefrom. The present invention further relates to a kit product for use in such diagnostic methods.

BACKGROUND OF THE INVENTION

Majority of *Escherichia coli* does not cause diseases, but exists in intestinal tract of healthy human or animals without any causing particular diseases. However, some of *Escherichia coli* has pathogenicity, and thus causes gastrointestinal infectious diseases such as abdominal pain, vomiting, diarrhoea and the like, as well as non-gastrointestinal infectious diseases such as urethritis, cystitis, meningitides and the like. *Escherichia coli* that causes gastrointestinal infectious diseases orally develops infection to exhibit pathogenicity in intestinal tract. Thus, such *Escherichia coli* is designated as diarrhetic *Escherichia coli*, or as pathogenic *Escherichia coli* in its broader definition. Pathogenic *Escherichia coli* can be classified into the following 5 groups:
1) Enterotoxigenic *Escherichia coli* (ETEC);
2) Enteroinvasive *Escherichia coli* (EIEC);
3) Enteropathogenic *Escherichia coli* (EPEC);
4) Enterohemorrhagic *Escherichia coli* (EHEC); or Verotoxin-producing *Escherichia coli* (VTEC);
5) Enteroadherent *Escherichia coli* (EAEC).

O-157:H7 (hereinafter referred to as merely "O-157") belongs to Enterohemorrhagic *Escherichia coli*. O-antigens have been classified into 1 to 173 types according to the differences of antigenic structures of lipopolysaccharides (LPS) that are residing on cell surfaces, while H-antigens have been classified into 1 to 57 types according to the differences of antigenic structures of flagellum. O-157 has eminently potent infectivity among causative microbes of food poisoning, thus approximately 60-80% of Enterohemorrhagic *Escherichia coli* is responsible for O-157. Although many of the causative microbes of food poisoning do not cause food poisoning unless from hundred of thousands to a million of cells were ingested, O-157 can result in onset of food poisoning with only several tens to several hundreds of cells. Latent period of food poisoning caused by O-157, i.e., from 4 to 10 days, is considerably long compared to those caused by the general causative microbes. Upon infection by O-157, symptoms such as diarrhoea, nausea, abdominal pain or the like, which are not distinguishable from the cases in common food poisoning, may be often developed. Further, in some cases, such symptoms as in common cold may be presented, in which disease states for example, fever, infectious manifestation in upper respiratory tract may be caused.

Verotoxin that is produced by O-157 (hereinafter referred to as "VT"; toxin which leads to lethal changes in Vero cells that are derived from renal tubular cells of African green monkey) is a similar toxin to *Shigella dysenteriae* toxin. VT consists of subunit A and subunit B, wherein subunit A exhibits a toxic activity, while subunit B is a part that exhibits a binding activity to mucous membranes. Genetically, VT is revealed to comprise at least 6 types, however, verotoxin 1 (hereinafter referred to as "VT1"; a toxin having almost identical amino acid sequence with that of *Shigella dysenteriae* toxin; MW: about 70,000) and verotoxin 2 (hereinafter referred to as "VT2"; a toxin having about 60% homology to *Shigella dysenteriae* toxin; MW: about 46,000) are predominantly involved in human infections. There are three types of O-157, i.e., one producing only VT1, other producing only VT2, and another producing the both. Among these types, the last type that produces both of the toxins is known to exist in a relatively large extent.

After O-157 invades into human gastrointestinal tract, it resists against gastric acid of pH 2-3, followed by early-stage colonization on epithelial cells of large intestine. Then, the bacteria externally secrete a gene product of attaching and effacing B (eae B) to colonize on cell surfaces via intimin, a gene product of eae A. This process is proposed as an attaching and effacing (A/E) lesion model [Ken-ichi Nagayama et al, Emerging infectious disease; *Journal of the Japanese Society of Internal Medicine* 86(11), 37, 1997]. VT binds to a Gb3 (a neutral glycolipid called globotriaosylceramide, having a structure of galactose α1-4 galactose β1-4 glucose-ceramide) receptor [Newburg, D. S. et al, *J. Infect Dis.*, 168, 476, 1993], thereafter, it is incorporated within the cells via a coated vesicle, and then transported to endplasmic reticulum by an intracellular membrane transportation system (a trans-Golgi network) [Sandvig, K. et al., *Nature*, 358, 510, 1992]. Next, subunit A moves into cytoplasm passing through a lipid bilayer to exert the toxicity. The subunit A of VT has the same RNA N-glycosidase activity as of ricin, i.e., a potent phytotoxin which is derived from seeds of *Ricinus communis*. It can hydrolyse an N-glycoside bond of adenosine from 5'-end at 4324th of 28S ribosome that is a member of 60S ribosome of eucaryote. Consequently, binding of aminoacyl tRNA to ribosome is inhibited, leading to cell deaths through inhibition of the protein synthesis. Moreover, it is also reported that subunit A is hydrolysed to be degraded into A1 and A2 during a transportation step predominantly to a trans-Golgi network, thus resulting in enhancement of the activity (Garred, O. et al., *Exp. Cell Res.*, 218, 39, 1995).

Approximately 10% of enterohemorrhagic colitis may be accompanied by serious complications such as hemolytic uremic syndrome (hereinafter referred to as "HUS"), thrombotic thrombocytopenic purpura, encephalopathy and the like. HUS is an acute renal failure commonly developed during infantile period as a manifestation of thrombotic microangiopathy. Although the cause of this disease may involve enterohemorrhagic colitis, infection by pneumococci, inheritance, drug, collagen disease or the like, HUS involved in infection by O-157 has been most frequently observed. In particular, vascular endothelial cells of renal microartery, capillary of glomerulus or the like may be compromised. In addition, central neuropathy in HUS stands the first of the cause of death for HUS these days. It is reported that upon intravenous administration of VT to an animal, vascular endothelial disorder of cerebrum and cerebellum, and disorder of Purkinje cellular injury may be resulted, as well as edema and hemorrhage of nerve cells in brain stem or spinal cord (Mizuguchi, M. et al., *Acta Neuropathol.*, 91, 254, 1996; Fujii, J. et al., *Infect Immun.*, 62, 3447, 1994; and Fujii, J. et al., *Infect Immun.*, 64, 5043, 1996). Accordingly, the cause may be speculated to be involved in direct or indirect influences on nerve cells, glial cells or the like through edema of vascular endothelial cells, narrowing of intravascular hollow space, platelet thrombi, fibrin thrombi, and/or further disruption of vascular brain barrier by VT.

Main factor of vascular endothelial disorder in HUS is assumed to be VT, an extracellular toxin. Among the VTs, VT2 has been known to be involved in the onset of more serious HUS (Ostroff, S. M. et al., *J. Infect. Dis.*, 160, 994-998, 1989). However, in recent years, cytokines such as tumor necrosis factor (TNF-α), interleukin 10 (IL-1β or the like, which were produced from monocytes, macrophages, vascular endothelial cells and the like due to VT or intracellular toxin, i.e., lipopolysaccharides (LPSs), were reported to bear an important role in establishment of vascular endothelial cellular disorder (Setten, P. A. et al., *Blood*, 88, 174, 1996; and Tesh, V. L. et al., *Infect Immun.*, 62, 5085, 1994). It is also reported that blood concentrations of TNF-αA and IL-1β in HUS patients during an acute phase were actually increased, and that blood TNF-α content was elevated during early stage of onset of diarrhoea in patients having VT detected in their stool (Lopez, E. L. et al, *Pediatr. Infect Dis. J*, 14, 594, 1995; Kar, N. C. et al., *Nephron*, 71, 309, 1995; and Inward, C. D. et al., *Arch. Dis. Child*, 77, 145, 1997).

Cytokines such as TNF-α IL-1β and the like cooperate with VT or LPS to activate polymorphonuclear leukocytes, and then accelerate their adhesion onto the vascular endothelial cells, thus resulting in disorder of vascular endothelial cells through release of active oxygen or elastase (Kar, N. C. et al., *Behring Inst. Mitt.*, 92, 202, 1993; Morgi, M. et al., *Blood*, 86, 4553, 1995; Fitzpatrick, M. M. et al., *Pediatr Nephrol.*, 6, 50, 1992; and Forsyth, K. D. et al., *Lancet*, 2, 411, 1989). Additionally, the expression of Gb 3 on vascular endothelial cells is increased to several hundreds folds to potentiate VT susceptibility by such actions of cytokines (Lopez, E. L. et al., *Pediatr Infect Dis. J*, 14, 594, 1995; Kaye, S. A. et al., *Infect Immun.*, 61, 3886, 1993; Keusch, G. T. et al., *J. Infect Dis.*, 173, 1164, 1996; and Forsyth, K. D. et al., *Lancet*, 2, 411, 1989). Furthermore, it is also reported that VT enhances the ability of leukocytes to adhere to cultured vascular endothelial cells (Morigi, M. et al., *Blood*, 86, 4553, 1995) and facilitates the production of endothelin (Bitzan, M. M. et al., *J. Clin. Ivest.*, 101, 372, 1998), and thus, glomerular vascular endothelial cells that were administered with VT are compromised by peripheral leukocytes (Mahan, J. D. et al., *3rd International Symposium and Workshop on Shiga Toxin-Producing E. coli infections*, p 83, Baltimore, 1997). In other reports, VT is assumed to cause necrosis (Obrig, T. G. et al., *Infect Immun.*, 56, 2373, 1988), apoptosis (Laurence, J. et al., *Semin. Hematol.*, 34, 98, 1997), acceleration of platelet aggregation by a von Willbrand factor (Moake, J. L. et al., *Blood*, 64, 592, 1984), reduction of producibility of prostaglandin 12 (Karch, H, et al., *Microb. Pathog.*, 5, 215, 1988), deposition of fibrin onto vascular endothelial cells (Menzel, D. et al., *Ann. Hematol.*, 68, 43, 1994), proliferation of mesangial cells and impairment of NO production (Dietrich, D. et al., *J. Am. Soc. Nephrol.*, 1, 609, 1990) and the like, leading to onset of HUS.

DISCLOSURE OF THE INVENTION

To date, VT has not been reported as being detected in blood of patients infected with O-157. VT entered into blood stream rapidly disappears following incorporation into vascular endothelial cells and the like. Therefore, VT in blood has been believed to be undetectable. Although a number of methods for the examination/diagnosis of infections by enterohemorrhagic *E. coli* have been developed so far, these methods are accordingly directed to fecal tests.

For example, kits are commercially available, including O-157 verotoxin gene-directed examination kit (Takara Shuzo Co., Ltd.) where VT from pathogenic *E. coli* O-157 is detected by a method in which PCR is utilized, as well as *E. coli* O-157 VIP 10 minutes detection kit (Gunze Sangyo, Inc.), Petri film (3M Health Care Limited), BAX System (Qualicon, Inc.), a kit produced by Difco, U.S.A. (available from Wako Pure Chemical Industries, Ltd.), a kit allowing detection within 48 hours (MERCK Japan Ltd.), pathogenic *E. coli* O-157 examination kit, TECRA (SCETI CO., LTD.), Reveal O-157:H7 examination kit (AR BROWN CO., LTD), Wellcolex *E. coli* O-157 (International Murex Technologies Corporation), GenePath system (Nihon Bio-Rad Laboratories Inc.), O-157 examination kit (ATC Corporation, Pasadena, Calif., USA). Such examination system in which faeces samples are tested as specimens can be generally classified into rapid diagnoses, definite diagnoses, and genetic diagnoses. Although detailed explanation of each of the diagnoses follows below, any of which has some drawbacks.

Known rapid diagnostic procedures for infectious diseases by enterohemorrhagic *E. coli* include EIA methods, immunochromatographic methods and latex methods, where detection of O-antigen is intended. However, any of which methods are problematic in sensitivity of detection. Furthermore, non-specific reaction with *Citrobacter freundii, Escherichia hermannii, Hafnia alvei*, and the like that reside in faeces may be observed. In addition, reaction with other VT-nonproducible microbes may be observed. Therefore, affirmative grounds for definite diagnoses can not be provided. Meanwhile, direct detection of VT from the faeces using EIA techniques are also attempted, however, drawbacks are not avoided such as impossible discrimination of VT1 and VT2, and limited detection of the faeces only in early stage of infection.

For a definite diagnosis of infectious diseases by enterohemorrhagic *E. coli*, two steps are required: isolation of microbes; and identification of VT-producing strain of thus isolated microbes. Examples of medium employed for the isolation of microbes include sorbitol-MacConkey (SMAC) agar medium, SIB (Sorbitol IPA Bile Salts) agar medium and CT-SMAC agar medium, namely, SMAC agar medium added with cefixime and potassium tellurite. Moreover, selection medium where rainbow agar or chromo agar is used may be included. Verification of the producibility of VT for thus selected microbes would be necessary. The methods for the verification employed may include latex aggregation techniques and EIA techniques in which immunological reaction is utilized, or methods in which PCR reaction is utilized. However, such methods where culture is involved require lengthy term, which may lead to dangers of the progress of the pathological states until the results of the diagnosis are revealed. Additionally, these methods are not practical because of the burdens in operation. Furthermore, in the current status, O157 has not been actually isolated in many of the hospital laboratories, and only a few facilities have anti-pathogenic *E. coli* immune serum all the time.

Besides, direct detection from stool by PCR methods, detection from the culture of the microbes, and identification of a VT-producing strain among the isolated *E. coli* have been carried out for the genetic diagnosis of the infectious diseases by enterohemorrhagic *E. coli*. A lot of inhibitory substances of PCR reaction are present in faeces, therefore pretreatments are necessary, which make the operation complicated. Moreover, methods for the quick detection of verotoxin-producing bacteria by DNA probe methods, fluorescence polarization methods where biosensor techniques are applied in which differences in DNA sequences of the bacterial DNA are detected through irradiation of fluorescence have been developed. However, satisfactory consequences have not been achieved yet.

Accordingly, clinical physicians have strongly desired the established methods which allow a rapid diagnosis of enterohemorrhagic E. coli infection in a convenient manner.

Meanwhile, HUS due to enterohemorrhagic E. coli is often developed within several days to two weeks from the onset of diarrhoea and/or hemorrhagic stool. In addition, cases have been reported where severe complications are developed without intensive manifestation of enterohemorrhagic colitis, and thus making anticipation and early finding of severe complications difficult. Further, owing to the absence of therapeutic methods of HUS which are fundamental and specific, cases where dialysis is necessary because of anuria, or cases where encephalopathia is accompanied may occur. Consequently, early diagnosis of HUS has been mandatory.

Present diagnoses of HUS in our country have been carried out on the basis of three cardinal signs: haemolytic anaemia (anaemia accompanied by appearance of fragmented red blood cells; Hb: not more than 10 g/dL), decrease in platelet number (platelet number of not more than 100 million/μL), and acute renal dysfunction (oliguria, anuria, or elevation of serum creatinine to not less than 1.5 fold of standard value of creatinine suited to the age). However, some HUS may be accompanied by the three cardinal signs, while other HUS may not. Accordingly, current diagnoses have been carried out taking into account of other concomitant clinical signs (e.g., hepatic dysfunction, pancreatitis, oliguria, edema, ecchymoses, headache, somnolence, restlessness, haematuria, proteinuria, convulsion, consciousness disorder and the like; as well as reduction in haptoglobulin value, elevation of LDH, elevation of serum bilirubin value, decrease in red blood cell number, decline of haemoglobin haematocrit, serum BUN (not less than 30 mg/dl), elevation of GOT and GPT in biological blood test).

Predominant renal disorders in HUS involve disorder of glomerular vascular endothelia. In addition to direct impairment of renal tubule by VT (Takeda, T et al., *J. Infect.*, 27, 339, 1993), VT, LPS or various types of cytokines are presumed to evoke renal disorder by possibly accelerating cytokine production via autocrine from glomerular vascular endothelial cells and renal tubular cells, or via paracrine (Kohan, D. et al., *3rd International Symposium and Workshop on Shiga Toxin-Producing E. coli infections*, p 81, Baltimore, 1997). On the basis of such information, VT and LPS are assumed to act on cytokine-producing cells such as macrophage, leukocyte and the like in vivo, and thus promote the production of various kinds of cytokines to impair vascular endothelial cells (particularly in kidney) additively or synergistically with the cytokine produced. Therefore, HUS resulting from O-157 is envisaged to occur by implicated several factors.

Consequently, even when only VT is detected, the results are far from being utilized for the diagnosis of renal disorder and HUS. There thus existed strong desires among the clinicians for methods that allow quick diagnoses as to whether or not the patients suffering from O-157 infection will advance to HUS, or methods for selecting the patients to be subjected to intensive care. Furthermore, in order to prevent the progress of enterohemorrhagic E. coli infection toward serious medical condition, methods for early finding of the manifestation of the deteriorated renal function resulting from the exposure to toxins have been long desired.

The present inventors thoroughly investigated the availability of substances present in urine as a parameter for the indication of the infection by enterohemorrhagic E. coli taking into account of impossible detection of VT from blood. Accordingly, it was found that the infection by enterohemorrhagic E. coli could be quickly diagnosed through using AQP2 that was excreted into urine as a parameter. In addition, correlation between the amount of the VT2 that was exposed and the amount of AQP2 excreted into urine was found, thereby resulting in a finding that the amount of the VT2 that was exposed can be indirectly determined by measuring the amount of AQP2 in urine. Moreover, because renal disorders are known to be caused by VT2, quick diagnoses of severity of renal disorder and/or renal dysfunction can be also carried out by measuring the amount of AQP2 in urine. Furthermore, because the amount of the VT2 that was exposed correlates to systemic symptoms, a quick diagnosis of transition to HUS can be also achieved by measuring the amount of AQP2 in urine.

Therefore, the present invention provides a method for diagnosing renal disorder comprising: detecting the excretion of AQP2 and/or molecules derived therefrom into urine or determining the amount of the excretion of the same into urine of a subject; and diagnosing morbidity of said subject for a renal disorder. As shown in the examples of the present invention, the measurement of the amount of urinary excretion of AQP2 allows more accurate and quick observation of significant differences between patients and healthy persons, compared to known parameters of renal disorder (β2-microglobulin, N-acetyl-β-D-glucosaminidase, urine creatinine, blood urea and nitrogen, serum creatinine, and the like). Therefore, a quick diagnosis of morbidity of renal disorder is allowed by detecting urinary excretion or determining the amount of excretion of AQP2. Determination of the amount of AQP2 in urine may be performed directly using the urine as a sample, otherwise may be performed following the isolation of AQP2 from urine.

Moreover, the present invention provides a method for diagnosing hemolytic uremic syndrome comprising: detecting the excretion of AQP2 and/or molecules derived therefrom into urine or determining the amount of the excretion of the same into urine of a subject; and diagnosing morbidity of said subject for hemolytic uremic syndrome. According to this method, a quick diagnosis of hemolytic uremic syndrome is achieved, which was difficult heretofore, according to this method.

The present invention further provides a method for diagnosing enterohemorrhagic E. coli infection comprising: detecting the excretion of AQP2 and/or molecules derived therefrom into urine or determining the amount of the excretion of the same into urine of a subject; and diagnosing enterohemorrhagic E. coli infection in said subject. In accordance with this method, a quick diagnosis of enterohemorrhagic E. coli infection, in particular, infection by E. coli that is a VT2 producing strain can be accomplished, and thus enabling therapy suited to enterohemorrhagic E. coli infection such as VT-producing strain, particularly VT2-producing strain or O-157:H7 and the like, without needs for awaiting the culture period of the bacteria to give the results of detection of VT2. Further, infection by E. coli that produces VT1 can also be quickly diagnosed.

Yet another aspect of the present invention is to provide a method for diagnosing severity of the aforementioned three kinds of diseases through the use of the amount of excretion of AQP2 and/or molecules derived therefrom into urine.

Higher amount of excretion of AQP2 into urine of a subject indicates more severe states of these diseases thereby allowing the diagnosis of the severity.

In the method described above, the detection of excretion of aquaporin 2 and/or molecules derived therefrom into urine, and the determination of the amount of excretion thereof may be carried out by an immunological procedure, preferably by an ELISA technique.

In addition, the present invention provides a method for the examination of renal function comprising: detecting the excretion of AQP2 and/or molecules derived therefrom into urine or determining the amount of the excretion of the same into urine of a subject; and evaluating renal function of said subject. This method is based on the event of increase in the amount of excretion of aquaporin 2 into urine concomitant with the lowered renal function. Thus, detection and determination of aquaporin 2 and/or molecules derived therefrom may be carried out by for example, the immunological procedure described above utilizing anti-aquaporin 2 antibodies, preferably by an ELISA technique.

The present invention further provides a kit for the diagnosis used in the aforementioned methods for the diagnoses, which comprise an anti-aquaporin 2 antibody. The kit of the present invention enables quick and accurate diagnoses of the diseases described above.

BRIEF DESCRIPTION OF THE DRAWINGS

FIG. 2 is a graph showing influences on osmotic pressure of urine by the administration of VT2 to rats.

BEST MODE FOR CARRYING OUT THE INVENTION

Figure 1:
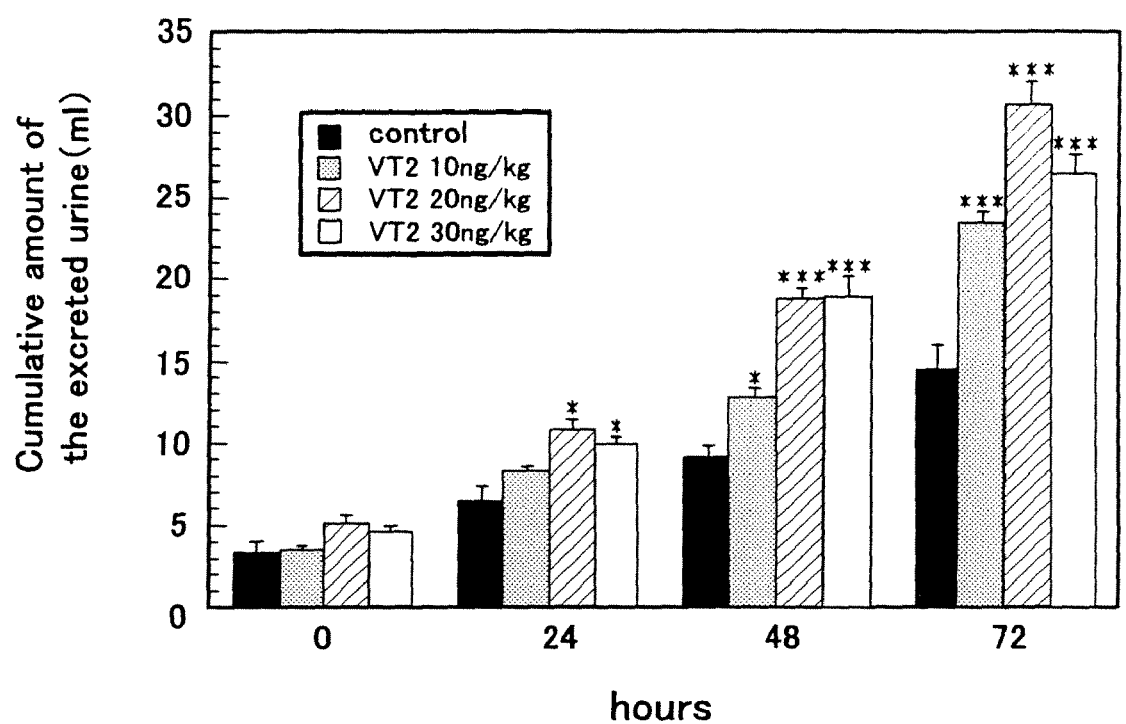
FIG. 1 is a graph showing influences on the amount of urinary excretion by the administration of VT2 to rats.

In 1992, Preston et al., cloned cDNA of CHIP28 (Channel like membrane intrinsic protein of 28 kDa) abundantly present in erythrocyte membrane. The protein was expressed in platanna ovule to demonstrate that CHIP 28 is a water channel that specifically allows the passage of water (Preston, G. M. et al., Proc. Natl. Acad. Sci. USA., 88, 11110, 1991, Preston, G. M. et al., Science, 256, 385, 1992). Analogous proteins were successively identified thereafter, and thus the existence of a gene family was revealed. These water channels are structurally and functionally similar, therefore, they are called as aquaqporin (hereinafter referred to as "AQP") family (Agre, P. et al., Am. J. Physiol., 265, 1993). AQPs belong to a group of membrane proteins referred to as MIP (Major intrinsic protein) family. Proteins in MIP/AQP family consist of approximately 270 amino acids, which are membrane proteins that penetrate the cell membrane 6 times. Further, two NPA box sequences are conserved having three amino acids, asparagine (A), proline (P), alanine (A) sequentially connected. Additionally, the aminoacid sequence has a high homologous region in its anterior part and latter part. AQPs have been found their existence in *E. coli*, plants, amphibian, and mammals and the like to form a AQP family (Chrispeels, M. J. et al., TIBS, 19, 421, 1995, Park, L. H. et al., J. Membr. Biol., 153, 171, 1996).

In mammals, at least 9 kinds of aquaporins have been cloned to date. Expression of APQs is found ubiquitously in whole body: AQP0 is expressed in crystalline lens of eyes; AQP1 in proximal renal tubule, descending limb of Henle's loop, brain choroid, gallbladder, eye, capillary endothelium; AQP2 in membrane of collecting tubule lumina; AQP3 in membrane of collecting tubule lumina, large intestine, small intestine, brain choroid, eye; AQP4 in collecting tubule, brain, eye, lung; AQP5 in salivary gland, eye, bronchus; AQP6 in kidney; AQP7 in testis, sperm; and AQP8 in testis, sperm, liver.

In particular, 4 kinds of AQPs exist in kidney, which participate in reabsorption of water. AQP1 exists on both of the membranes: epithelial cellular luminal membrane of renal tubule; and basolateral membrane, of proximal renal tubule and descending limb of Henle's loop. In principal cells of collecting tubule, AQP2 and AQP3 exist, and particularly, AQP2 exists on luminal membrane and on vesicular membrane of cells immediately beneath the luminal membrane, while AQP3 exists on basolateral membrane. Accordingly, reabsorption of water is believed to be performed starting from AQP2 on luminal membrane of the principal cells via AQP3 on luminal membrane. AQP4 has been reported to predominantly exist in basolateral membrane of collecting tubule, papillary area of collecting tubule.

The present inventors provide, through detection of excreted AQP2 and/or molecules derived therefrom into urine, methods for diagnosing infection by enterohemorrhagic *Escherichia coli*, an early diagnosis of HUS, and diagnosing the severity of renal dysfunction and renal disorder.

Enterohemorrhagic *Escherichia coli* used herein comprises enterohemorrhagic *Escherichia coli* (EHEC) and verotoxin-producing *Escherichia coli* (VTEC).

AQP2 referred to herein means a mature form or an intact form of AQP2, and molecules derived therefrom mean precursors of AQP2, i.e., precursors of AQP2 comprising a signal sequence, fragments, i.e., fragments comprising a part of extracellular domain of AQP2; fragments comprising a part of transmembrane domain of AQP2; and fragments comprising a part of intracellular domain of AQP2, as well as variants thereof, i.e., AQP2 having substitution, addition, insertion and/or deletion of one or more amino acid(s) of the amino acid sequence of AQP2 protein by the mutation of AQP2 gene. For a reference, mutation of amino acid sequence resulting from the mutation of AQP gene has been found at least 13 positions to date (Saishin Igaku, 52, 8, 1806-1811, 1997).

As the diagnostic methods of renal disorder, hemolyticuremic syndrome, or enterohemorrhagic *E. coli* infection, wherein excretion of AQP2 and/or molecules derived therefrom into urine is detected, or the amount of excretion thereof is determined, processes in which immunological binding property is utilized (e.g., peptide antibodies, polyclonal antibodies, monoclonal antibodies or the like to AQP2, preferably to human AQP2) may be used. In this process, the above-described antibodies can be used preferably in immunoblotting, affinity chromatography, immunoprecipitation or ELISA. Moreover, these diagnostic methods may further comprise a step of isolating AQP2 and/or molecules derived therefrom based on the process in which similar immunological binding properties are utilized.

Examples of process for detecting or quantitatively determining AQP2 and/or molecules derived therefrom using antibodies may include methods of measuring AQP2 and/or molecules derived therefrom in a sample utilizing, for example, sandwich techniques in which a sandwich complex is detected which was produced by subjecting AQP2 and/or molecules derived therefrom to a reaction with an antibody coupled to an insoluble support and a labeled antibody; otherwise, competitive techniques in which AQP2 and/or molecules derived therefrom in a sample is/are measured by subjecting labeled AQP2 and/or molecules derived therefrom, and AQP2 and/or molecules derived therefrom in a sample to a competitive reaction with the antibody followed by the measurement of the amount of the labeled antigen that reacted with the antibody.

Furthermore, the process for isolating AQP2 and/or molecules derived therefrom using these antibodies may include, for example, affinity chromatography by means of a support coupled to the antibody described above, and/or immunoprecipitation, which may be suitably used for the isolation of AQP2 and/or molecules derived therefrom. Namely, affinity chromatography and/or immunoprecipitation by column procedures, batch procedures and the like may be conducted, which comprises the steps of allowing a specific interaction between an antigen and an antibody through contacting a test solution with a support coupled to the antibody described above; then washing the support and eluting bound AQP2 and/or molecules derived therefrom.

Upon the measurement of AQP2 and/or molecules derived therefrom by the sandwich ELISA technique, two-step methods in which AQP2 and/or molecules derived therefrom is/are first subjected to a reaction with an immobilized antibody; thereafter, unreacted materials are completely removed by washes; and then a labeled antibody is added thereto, alternatively, one-step methods in which an immobilized antibody, a labeled antibody and AQP2 and/or molecules derived therefrom are mixed concurrently.

Insoluble support for use in the method described above include for example, synthetic resin such as polystyrene, polyethylene, polypropylene, polyvinyl chloride, polyester, polyacrylic acid ester, nylon, polyacetal, fluorine-contained resin and the like; polysaccharides such as cellulose, agarose and the like; glasses; metals; and the like. The insoluble support may be in a variety of forms, for example, tray-like, spherical, fibrous, cylindrical, discal, vessel-like, cell-like, tubular, and the like. The support onto which the antibody had been adsorbed may be stored ad libitum in cold, in the presence of an antiseptic agent such as sodium azide and the like.

For the immobilization of the antibody, known chemical coupling processes or physical adsorption processes may be adopted. Chemical coupling process includes for example, processes in which glutaraldehyde is used; maleimide processes in which N-succinimidyl-4-(N-maleimidemethyl)cyclohexane-1-carboxylate and N-succinimidyl-2-maleimide acetate and the like; carbodiimide processes in which 1-ethyl-3-(3-dimethylaminopropyl)carbodiimide hydrochloride and the like is used. Other process includes maleimidebenzoyl-N-hydroxysuccinimide ester processes, N-succimidyl-3-(2-pyridylthio) propionic acid processes, bisdiazobenzidine processes, dipalmityl lysine processes. Alternatively, a complex that had been formed previously by subjecting the substance to be detected to a reaction with two kinds of antibodies of which epitopes are different can be captured with the third antibody to the antibody, which was immobilized as described above.

The material to be used for labelling may include enzyme, fluorescent materials, luminescence materials, radioactive materials, metal chelates and the like. Examples of enzyme may include peroxidase, alkaline phosphatase, β-D-galactosidase, malate dehydrogenase, *staphylococcus* nuclease, delta-5-steroid isomerase, α-glycerolphosphate dehydrogenase, triose phosphate isomerase, horseradish peroxidase, asparaginase, glucose oxidase, ribonuclease, urease, catalase, glucose-6-phosphate dehydrogenase, glucoamylase, acetylcholine esterase and the like. Fluorescent materials may include for example, fluorescein isothiocyanate, phycobilin protein, rhodamine, phycoerythrin, phycocyanin, allophycocyanin, orthophthalic aldehyde and the like. Luminescence materials may include isoluminol, lucigenin, luminol, aromatic acridinium ester, imidazole, acridinium salt and modified ester thereof, luciferin, luciferase, aequorin and the like. Radioactive materials may include $^{125}I$, $^{127}I$, $^{131}I$, $^{14}C$, $^{3}H$, $^{32}P$, $^{35}S$ and the like. These materials are not limited thereto as long as the material can be used in immunological determination methods. In addition, low molecular weight hapten such as biotin, dinitrophenyl, pyridoxal or fluorescamine may be conjugated to the antibody. Preferably, horseradish peroxidase may be used as a labelling enzyme. This enzyme can react with many kinds of substrates, which can be readily conjugated to the antibody by a periodic acid method.

When an enzyme is used as a labelling material, a substrate for measuring its activity, and a color-developing agent as needed may be employed. When peroxidase is used as the enzyme, $H_2O_2$ may be used as a substrate solution, and 2,2'-azino-di-[3-ethylbenzthiazolin sulfonate]ammonium (ABTS),5-aminosalicylic acid, orthophenylenediamine, 4-aminoantipyrine, 3,3',5,5'-tetramethylbenzidine or the like may be used as a color-developing agent. When alkaline phosphatase is employed as the enzyme, orthophenylphosphate, paranitrophenylphosphate or the like may be used as the substrate. Alternatively, when β-D-galactosidase is used as the enzyme, fluorescein-di-(β-D-galactopyranoside), 4-methyl-umbelliferyl-β-D-galactopyranoside, or the like may be used as the substrate.

Available crosslinking agents include N,N'-orthophenylenedimaleimide, 4-(N-maleimidemethyl)cyclohexanoyl N-succinimide ester, 6-maleimidehexanoyl N-succinimide ester, 4,4'-dithiopyridine, and other known crosslinking agents. The reaction of such a crosslinking agent with the enzyme and the antibody may be conducted in accordance with known methods depending upon the properties of the respective crosslinking agents. Additionally, the antibodies to be used may be any fragments of the antibodies for example, Fab', Fab, F(ab')2 depending on the condition. Furthermore, enzymatically labelled antibodies may be prepared by using a similar process to any one of those for polyclonal antibodies and monoclonal antibodies. When the enzymatically labelled antibody that was obtained by using the aforementioned crosslinking agent is purified by any known methods such as affinity chromatography or the like, more sensitive immunological determination system can be achieved. The enzymatically labelled antibody that was purified in such a manner may be mixed with a stabilizer such as thimerosal, glycerol or the like, alternatively, may be lyophilized, and then stored in a cold and dark place.

Moreover, the present invention provides a kit for easy detection/measurement of AQP2 in urine. In particular, a primary antibody is coupled to an appropriate solid phase, then urine is contacted to the solid phase. Thereafter, a liquid is contacted, which comprises a secondary antibody labeled with an enzyme to a complex of the primary antibody and AQP2. Color development is then executed by contacting a liquid comprising a substrate for the enzyme to measure the concentration of AQP2 in urine by the color development.

EXAMPLE

The present invention is described in more detail by the following non-limiting illustrative examples. However, the present invention should not be construed to be limited to the examples, but confined only by the following claims.

Verotoxin (VT) used in the following examples is VT2 or VT1. Upon intravenous administration of VT1 to an animal, it is known that evident diseased renal states are not observed although anemia, decrease of platelets, brain disorder may occur. That is to say, in the experimental system wherein VT1 alone is used, causing a typical glomerular lesion of HUS to a laboratory animal is difficult. Therefore, such a system can be applied to an animal model of acute encephalopathy accompanied by HUS, however, it cannot be an animal model of HUS focused on renal disorder. (Strockbine, N. A. et al., Infect Immun., 53, 135, 1986, Yutsudo, T. et al., Microb. Pathog., 3, 21, 1987, Zoja, C. et al., J. Lab. Clin. Med., 120, 229, 1992, Richardson, S. E. et al., Infect Immun., 60, 4154, 1992). To the contrary, oral administration of VT2-producing EHEC to a laboratory animal makes it possible to cause typical diseased states in HUS such as diarrhea, hemorrhagic stool, anaemia, decrease of platelets, glomerular disorder, necrosis of renal tubule, central nervous system disorder and the like (Wadolkowski, E. A. et al., Infect Immun., 58, 3959, 1990, Zepada, H. M. et al., 3rd International Symposium and Workshop on Shiga Toxin-Producing *E. coli* infections, p 73, Baltimore, 1997, Valdivia-Anda, G. et al., 3rd International Symposium and Workshop on Shiga Toxin-Producing *E. coli* infections, p 70, Baltimore, 1997). Therefore, using VT2 rather than VT1 is believed to be more appropriate for establishing a HUS model.

Example 1

Preparation of Polyclonal Antibodies and Monoclonal Antibodies to AQP2

A peptide having cysteine at N-terminus of a peptide corresponding to 15 amino acids of C-terminus of human AQP2 amino acid sequence (Sasaki, S. et al., Clin. Invest., 93, 1250-1256, 1994), of which amino acid sequence is $NH_2$-Cys-Val-Glu-Leu-His-Ser-Pro-Gln-Ser-Leu-Pro-Arg-Gly-Thr-Lys-Ala-COOH (SEQ ID NO: 1) was synthesized by a standard solid phase peptide synthesis process (Carpino, L. A. et al., J. Org. Chem., 37, 3404-3409, 1972). The synthetic peptide was then purified by a HPLC method, and the resultant peptide was mixed with maleimide-activated keyhole limpet hemocyanin that binds to the N-terminal cysteine. 0.1 mg of the synthetic peptide was mixed with Ribi adjuvant (Ribi ImmunoChem Research, Inc.), and 1.0 mL of the mixture was infused subcutaneously and intracutaneously to a female New Zealand white rabbit. On every 14 days, 1.0 mL of the same mixture was administered as a booster. After the fourth booster was administered, a rabbit was obtained having an anti-human AQP2 antiserum of which titer being a ratio of 1:16,000 or more by ELISA. Thus, the following examples were conducted using the antiserum of the rabbit. The antiserum was purified on a protein G affinity column A monoclonal antibody to human AQP2 was prepared by: mixing 20 μg of the synthetic peptide set out in SEQ ID NO: 1 with Ribi adjuvant; infusing 0.2 mL of the mixture subcutaneously to a female BALB/c mouse; and administering subcutaneously 0.2 mL of the mixture subcutaneously as a booster on every 14 days. The fourth booster was performed by intravenously administering a mixture comprising 20 μg of the same synthetic peptide in saline. Spleen cells were fused with P3×63Aq8.653 myeloma cells, and the hybridoma was screened by EIA assay using the same peptide as an antigen.

Thus resulting monoclonal antibodies were purified on Protein G sepharose, and examined for the cross-reactivity with synthetic peptides corresponding to C-terminuses of rat and human AQP1, AQP2, AQP3, AQP4 and AQP5 by EIA assay. Consequently, the synthetic peptide corresponding to human and rat AQP2 reacted at 100%, whilst the reactivity with human and rat AQP1, AQP3, AQP4 or AQP5 was 0.01% or less. Table 1 below presents amino acid sequences of peptides corresponding to C-terminuses of human and rat AQP1, AQP2, AQP3, AQP4 and AQP5. Each of the synthetic peptide has cysteine at its N-terminus, which was synthesized by a standard solid phase peptide synthesis process and purified by HPLC method. (Halnann, S. et al., Am. J. Physiol. 274 (CellPhysiol. 43) C1332-C1345, 1998).

TABLE 1

Human aquaporin C-terminal peptide amino acid sequence

AQP1.  $NH_2$-Cys-Leu-Asp-Ala-Asp-Asp-Ile-Asn-Ser-Arg-Val-Glu-Met-Lys-Pro-Lys-COOH
       (SEQ ID NO: 2)

AQP2.  $NH_2$-Cys-Val-Glu-Leu-His-Ser-Pro-Gln-Ser-Leu-Pro-Arg-Gly-Thr-Lys-Ala-COOH
       (SEQ ID NO: 1)

TABLE 1-continued

AQP3.  NH₂-Cys-Glu-Glu-Glu-Asn-Val-Lys-Leu-Ala-His-
Val-Lys-His-Lys-Glu-Gln-Ile-COOH
(SEQ ID NO: 3)

AQP4.  NH₂-Cys-Glu-Lys-Lys-Gly-Lys-Asp-Gln-Ser-Gly-
Glu-Val-Leu-Ser-Ser-Val-COOH
(SEQ ID NO: 4)

AQP5.  NH₂-Cys-Glu-Pro-Asp-Glu-Asp-Trp-Glu-Glu-Gln-
Arg-Glu-Glu-Arg-Lys-Lys-Thr-Met-Glu-Leu-Thr-
Thr-Arg-COOH
(SEQ ID NO: 5)

Rat aquaporin C-terminal peptide amino acid sequence

AQP1.  NH₂-Cys-Leu-Asp-Ala-Asp-Asp-Ile-Asn-Ser-Arg-
Val-Glu-Met-Lys-Pro-Lys-COOH
(SEQ ID NO: 6)

AQP2.  NH₂-Cys-Val-Glu-Leu-His-Ser-Pro-Gln-Ser-Leu-
Pro-Arg-Gly-Ser-Lys-Ala-COOH
(SEQ ID NO: 7)

AQP3.  NH₂-Cys-Glu-Ala-Glu-Asn-Val-Lys-Leu-Ala-His-
Met-Lys-His-Lys-Glu-Gln-COOH
(SEQ ID NO: 8)

AQP4.  NH₂-Cys-Ile-Asp-Ile-Asp-Arg-Gly-Asp-Glu-Lys-
Lys-Gly-Lys-Asp-Ser-Ser-Gly-Glu-COOH
(SEQ ID NO: 9)

AQP5.  NH₂-Cys-Glu-Pro-Glu-Glu-Asp-Trp-Glu-Asp-His-
Arg-Glu-Glu-Arg-Lys-Lys-Thr-Ile-Glu-Leu-Thr-
Ala-His-COOH
(SEQ ID NO: 10)

Example 2

Determination of the Amount of Excretion of AQP2 into Urine by an Immunoassay

In order to determine the amount of excretion of AQP2 into urine, the concentration of AQP2 was measured using the rabbit anti-human AQP2 polyclonal antibody described above in Example 1 using urine from rats of the VT2-treated group or the untreated group as a sample.

VT2 and 0.1 weight/volume % of rat serum albumin (Sigma, St Louis, Mo.) dissolved in 100 µl of saline were intravenously injected to 4 weeks old female Wistar rats to constitute a VT2-treated group. Control group was made by intravenously injecting 100 µl of saline containing 0.1 w/v % of rat serum albumin. VT2 employed was obtained by the purification from a supernatant of *E. coli* C6000 culture (Yutsudo, T. et al., Microb. Pathogenesis, 3, 21-30, 1987).

Ten µL of the urinary sample collected from rats of each group was coated on a 96-well microplate to perform the EIA technique. Standard AQP2 was prepared in accordance with the method proposed by Kishore, B. et al., (Kishore, B. et al., Am. J. Physiol., 27, 1 (Renal Fluid Electrolyte Physiol. 40), F62-F70, 1996). Standard AQP2 was serially diluted to give 0 to 4,000 fmol/10 µL, and the same volume was added to each of the wells. Next, the wells were blocked by incubating with PBS (phosphate buffered saline) containing 0.5% casein. Thereafter, 50 µL of a solution of the above-described rabbit anti-human AQP2 antibody diluted to 1:1,000 in PBS containing 0.5% casein was added to each well to allow the reaction for 1 hour. The primary antibody was removed by washing the well, and then a reaction with horseradish peroxidase labeled goat anti-rabbit IgG+IgM (H+L), "F (ab') fragment", (×1,000 diluted) was allowed for 1 hour at room temperature. Unbound secondary antibody was removed by washing, and the immune complex product was visualized by the reaction with 0.1 M citrate buffer (pH 4.2) containing 0.01% $H_2O_2$, 2.2 mM o-phenylenediaminedihydrochloride for 15 minutes at room temperature. The enzyme reaction was stopped by adding 1N HCl, and then absorbance at 490 nm was measured with EIA multispectrometer. The measurements of the amount of AQP2 in urine were calculated on the basis of a standard curve for the standard AQP2. As a result, it was verified that the amount of AQP2 excreted into urine could be measured at a concentration ranging from 0 to 400 pmol/mL in urine from a rat treated with VT2.

Example 3

Determination of the Amount of Excretion of AQP2 into Human Urine by a Sandwich ELISA Technique Fifty µL of an anti-human AQP2 mouse monoclonal antibody (see, Example 1) diluted to 1,000 fold in PBS was bound on wells of an ELISA plate. After blocking the plate with PBS containing 0.5% casein, 50 µL of a human urinary sample diluted to 5 fold was added thereto. An antigen-antibody binding reaction was then allowed. Thereafter, purified rabbit anti-human AQP2 antibody and horseradish peroxidase labeled goat anti-rabbit IgG+IgM (H+L), "F (ab') fragment", (diluted to 1,000 fold) were added to subject to a reaction for one hour. The amount of AQP2 in the urine sample was determined by the similar procedure as in Example 2. Consequently, it was verified that the amount of AQP2 excreted into urine could be measured at a concentration ranging from 0 to 20 pmol/mL in urine from a human treated with VT2.

Example 4

Determination of the Amount of Excretion of AQP2 into Urine by a Western Blotting Technique Membrane fractions of rats treated with VT2 (similar to those in Example 2 above) and untreated rats were prepared in accordance with the method of Halnann et al., (Halnann, S. et al., Am. J. Physiol., 274 (Cell Physiol. 43), C1332-C1345, 1998). Kidney was homogenized in 10 mL of a dissociation solution (0.3 M sucrose, 25 mM imidazole, 1 mM EDTA, pH 7.2, 8.5 mM leupeptin, 1 mM phenylmethylsulfonylfluoride). The homogenate was centrifuged for 20 min. at 1,000×g to collect a supernatant for removing the nucleus, and then the supernatant was centrifuged for 20 min. at 100,000×g. Thus resultant pellet was resuspended in 10 mL of the dissociation solution described above, followed by the determination of protein concentration using Pierce BCA Protein Assay Reagent Kit (Pierse). The membrane fraction dissolved in a sample preparation solution (2% SDS, 65 mM Tris-HCl, 10% glycerol, 5% 2-mercaptoethanol) at 90° C. was separated on SDS-PAGE, and was transferred to a PVDF membrane (poly (vinylidenefluoride) membrane, Milipore Co., Ltd.,). The PVDF membrane was blocked with PBS containing 2% skimmed milk powder, and was subjected to a reaction with ×1,000 diluted, purified anti-human AQP2 rabbit antibody at room temperature for one hour. The membrane was thereafter washed three times with PBS, and subjected to a reaction with ×2,000 diluted horseradish peroxidase labeled goat anti-rabbit IgG+IgM (H+L) "F(ab)2 fragment" for one hour. After the secondary antibody was washed out, the resultant immune complex was visualized with 0.1 M citrate buffer (pH 6.0) containing 1.2 mM dimethyl-p-phenylenediamine/2.2 mM 4-chloro-1-naphthol. Consequently, bands corresponding to AQP2 (7.5 kDa, 14.4 kDa and 45 kDa) were identified.

Example 5

Influences on the Amount of Rat Urinary Excretion by an Intravenous Administration of VT2

To male Wister rats of four weeks old, intravenously administered 100 μl of VT2 of 10, 20 and 30 ng/kg weight (diluted in 100 μl of saline containing 0.1 weight/volume % of rat serum albumin (Sigma, St Louis, Mo.)). Thereafter, the excreted urine was collected using a metabolism cage to measure the amount thereof on every 12 hours. Accordingly, cumulative amount of the excreted urine was recorded over each time point of urine collection. In this experiment, VT2 was employed, which was obtained by the purification from a supernatant of E. coli.H7, C6000 strain (933w) culture according to a process disclosed in Yutsudo, T. et al., Microb. Pathogenesis, 3, 21-30, 1987.

The results are shown in FIG. 1, which indicate that total amount of urinary excretion tends to be elevated in the rat administered with 10 ng/kg of VT2, not more than the lethal dose that does not even result in findings of paralysis of extremities following the administration of the toxin, in comparison with the control rat at 24 hour after the administration of the toxin. The results further indicate that significant increase in the amount of urinary excretion was found after 48 hours of the administration and later. The amount of urinary excretion of the rat administered with 10 ng/kg of VT2 on one week after the administration returned to the normal level. When the rats intravenously administered with VT2 of greater than lethal dose (20 mg/kg, 30 ng/kg) were observed with time, paralysis of posterior limb appeared on 65 to 75 hours, followed by much more severe manifestation in proportion to the administered dose, leading to death. Besides, the amount of urinary excretion significantly increased in a time dependent manner and in dependence upon the amount of the administered VT2. Each average survival time of rats administered with 20 ng/kg and 30 ng/kg of VT2 was respectively 79.6+/−2.2 hrs and 68.8+/−0.9 hrs.

This experiment revealed that increase in the amount of urinary excretion and the deteriorated manifestation of whole body were caused in dependence on the amount of VT2 administered.

Example 6

Influences on the Osmotic Pressure of Rat Urine by an Intravenous Administration of VT2

Rats treated with VT2 in Example 5 were examined for changes in osmotic pressure of urine. The osmotic pressure was measured using a vapor-pressure osmometer (OM-6020, Kyotodaiichi Co., Ltd.)

Figure 2:
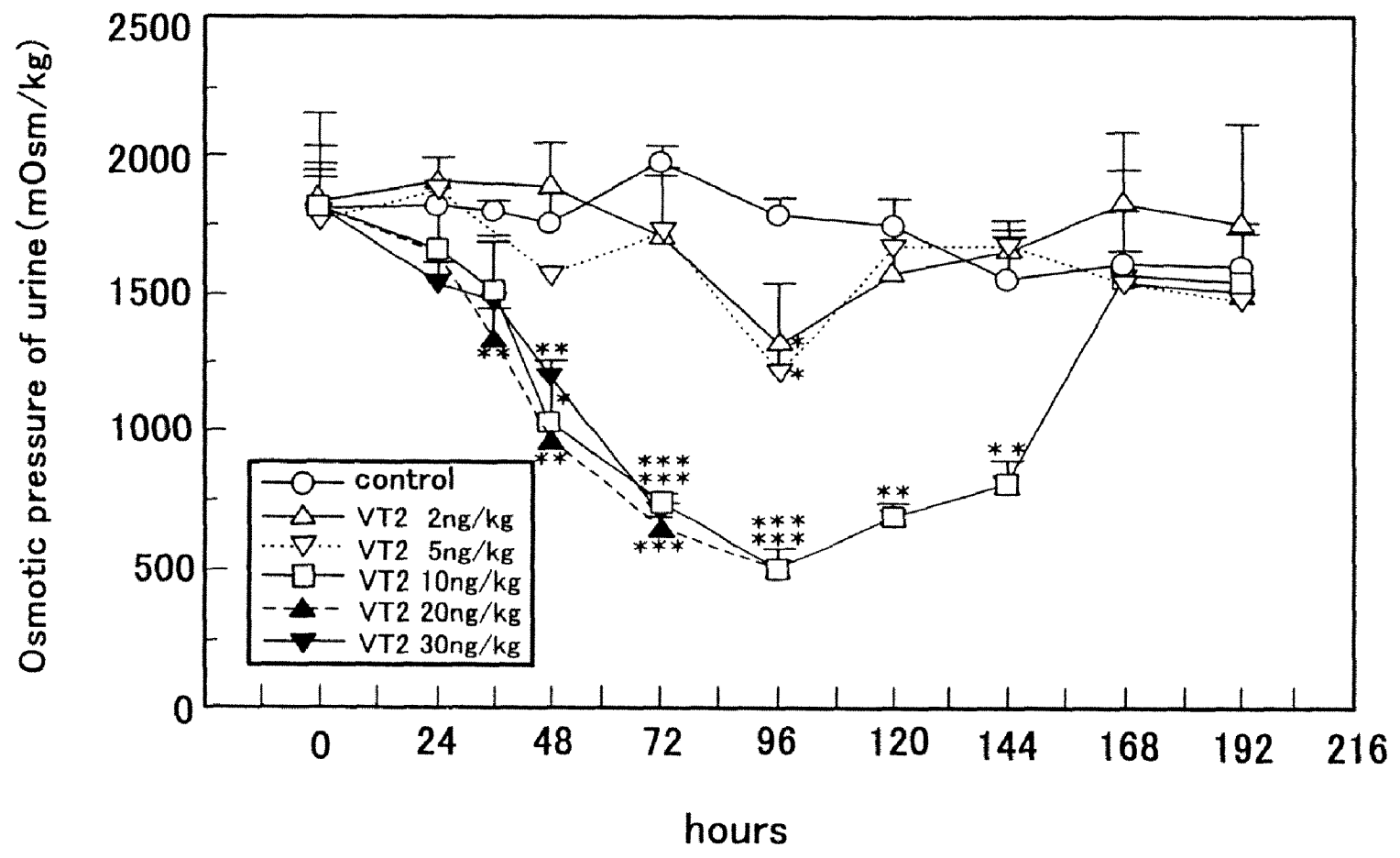

As a result, it was revealed that the urinary osmotic pressure of rats administered with 10, 20 and 30 ng/kg of VT2 decreased inverse relation to the increase in the amount of urinary excretion, and that the decrease of urinary osmotic pressure was dependent on the amount of the VT2 administered (FIG. 2). The urinary osmotic pressure of rats administered with VT2 (10 ng/kg) in an amount that caused no lethal action showed minimum pressure at 96 hours after the administration, such minimum pressure was corresponding to about 29% of that control rats.

Therefore, it was revealed that renal disorder was caused by the administration of VT2 through the increase in the amount of urine, which was accompanied by the lowered urinary osmotic pressure.

Example 7

Influences on Rat Kidney by an Intravenous Administration of VT2 (1)

Figure 3:
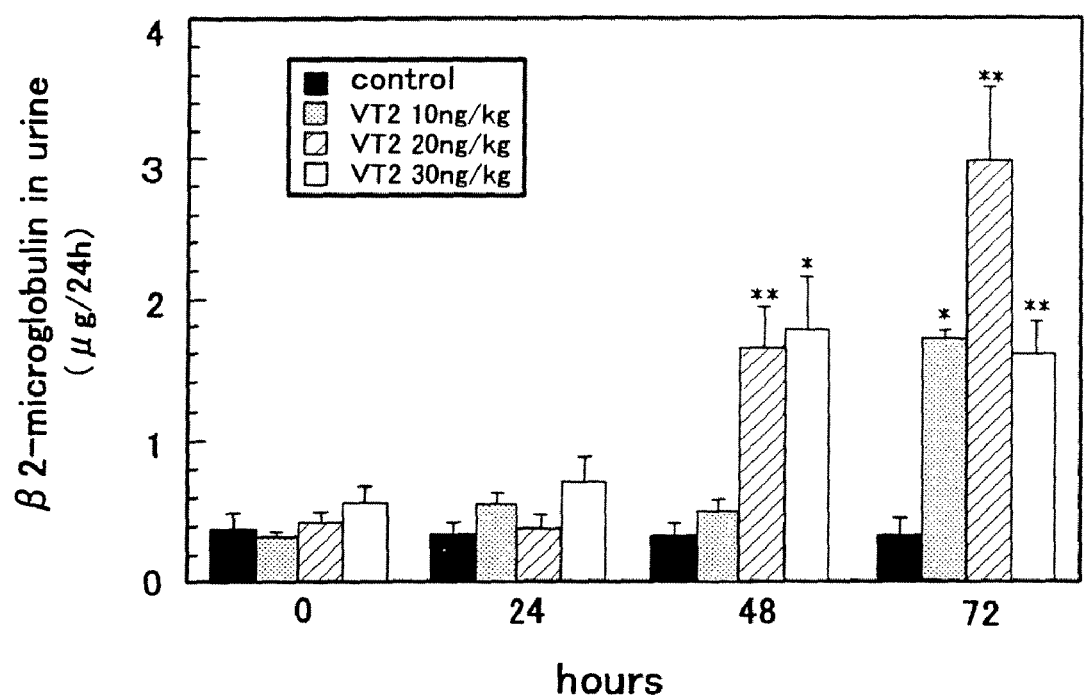
FIG. 3 is a graph showing time-dependent alteration of the amount of excretion of $\beta$2-microglobulin into urine for the verification of renal disorder caused by the administration of VT2 to rats.

In order to demonstrate whether the treatment with VT2 leads to renal disorder, the amount of β2-microglobulin excreted into urine was measured in VT2-treated rats described in Example 5 above (FIG. 3). The amount of β2-microglobulin excreted into urine was determined by EIA using rabbit anti-human β2-microglobulin antibody (Rockland, Gilbertsville, Pa.).

Consequently, the level of β2-microglobulin in the cumulative urine over 24 hours in rats treated with VT2 (20 ng/kg) on two days after the administration (24 to 48 hours) was significantly increased over the untreated control, and the level of β2-microglobulin reached to its maximum in the cumulative urine over 24 hours on three days after the administration (48 to 72 hours).

Example 8

Influences on Rat Kidney by an Intravenous Administration of VT2 (2)

Figure 4:
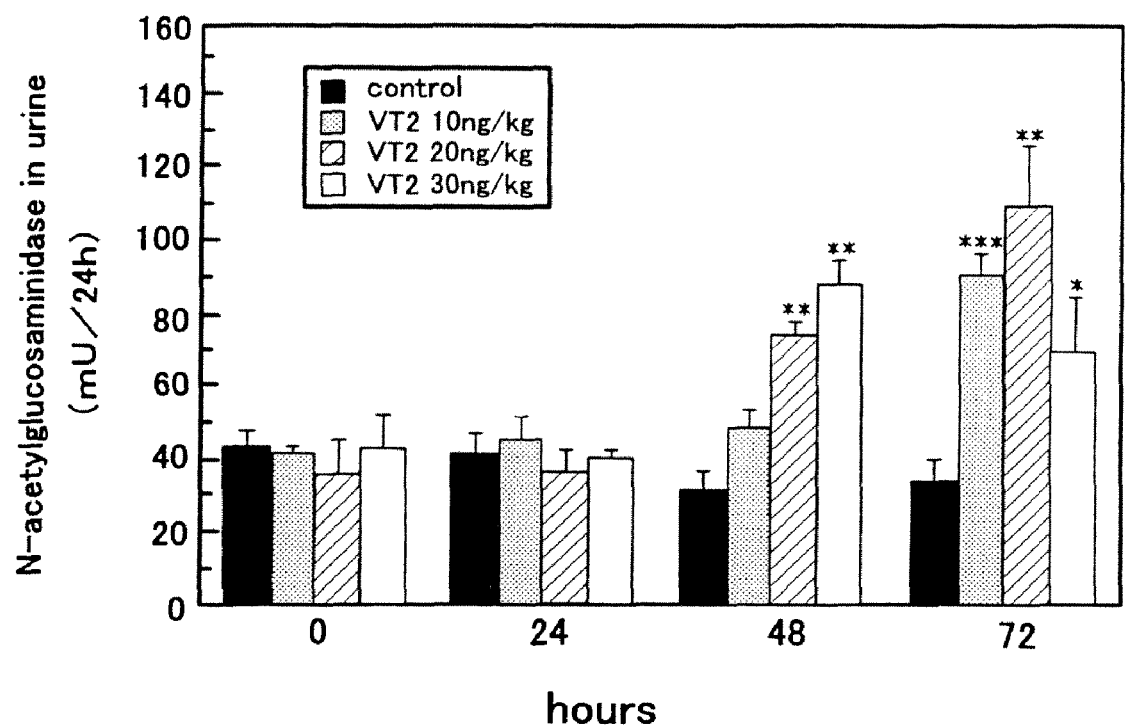
FIG. 4 is a graph showing time-dependent alteration of the amount of excretion of NAG into urine for the verification of renal disorder caused by the administration of VT2 to rats.

In order to further demonstrate the renal disorder by VT2, the amount of lysosome enzyme (N-acetyl-β-D-glucosamidase, hereinafter, referred to as "NAG") excreted into urine was measured in VT2-treated rats described in Example 5 above, which was believed to derive from collecting tubule cells. The amount of NAG was determined by measuring the activity of N-acetyl-β-D-glucosamidase using an assay kit, NAG Test Shionogi (Shionogi, Co., Ltd.) (FIG. 4).

The level of NAG in the cumulative urine over 24 hours in rats treated with VT2 (20 ng/kg) on two days after the administration (24 to 48 hours) was significantly increased, and the level of NAG reached to its maximum in the cumulative urine over 24 hours on three days after the administration (48 to 72 hours). In addition, the level of NAG in the cumulative urine over 24 hours on three days after the administration (48 to 72 hours) was also significantly increased at the dose of 10 ng,/kg.

Example 9

Influences on Rat Kidney Glomerulus by an Intravenous Administration of VT2

Figure 5:
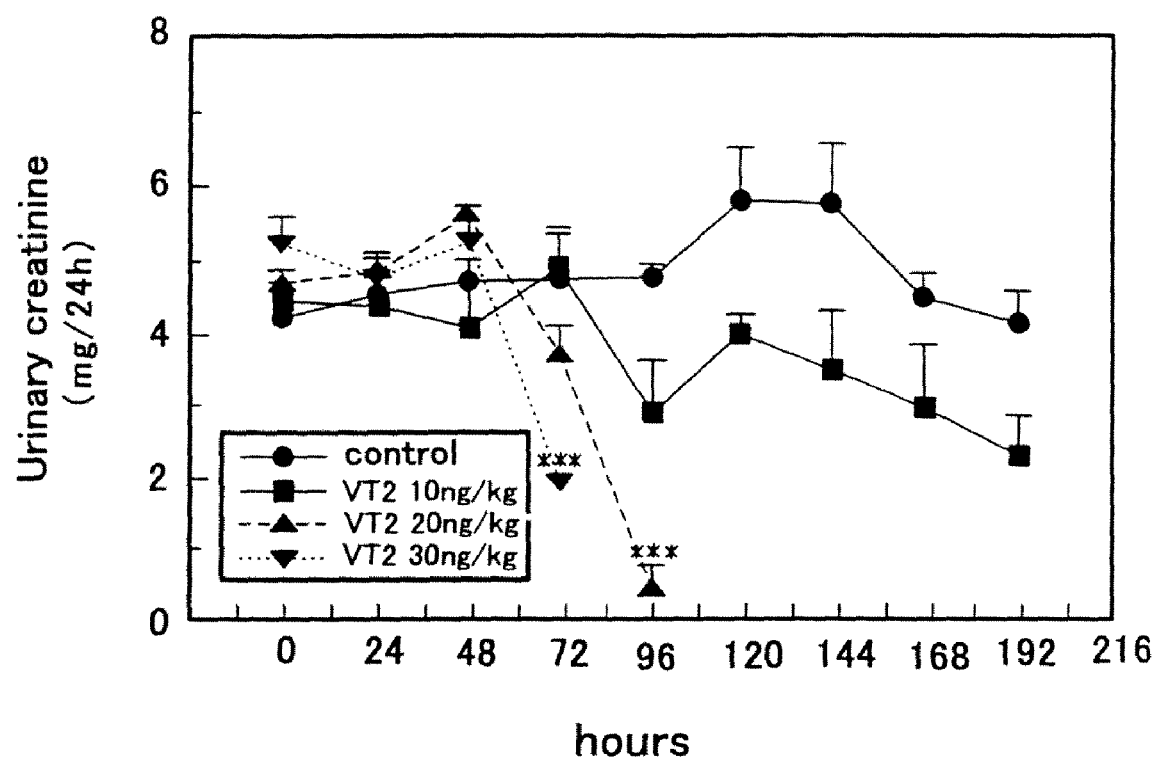
FIG. 5 is a graph showing time-dependent alteration of the amount of excretion of creatinine into urine for the verification of renal disorder caused by the administration of VT2 to rats.
Figure 6:
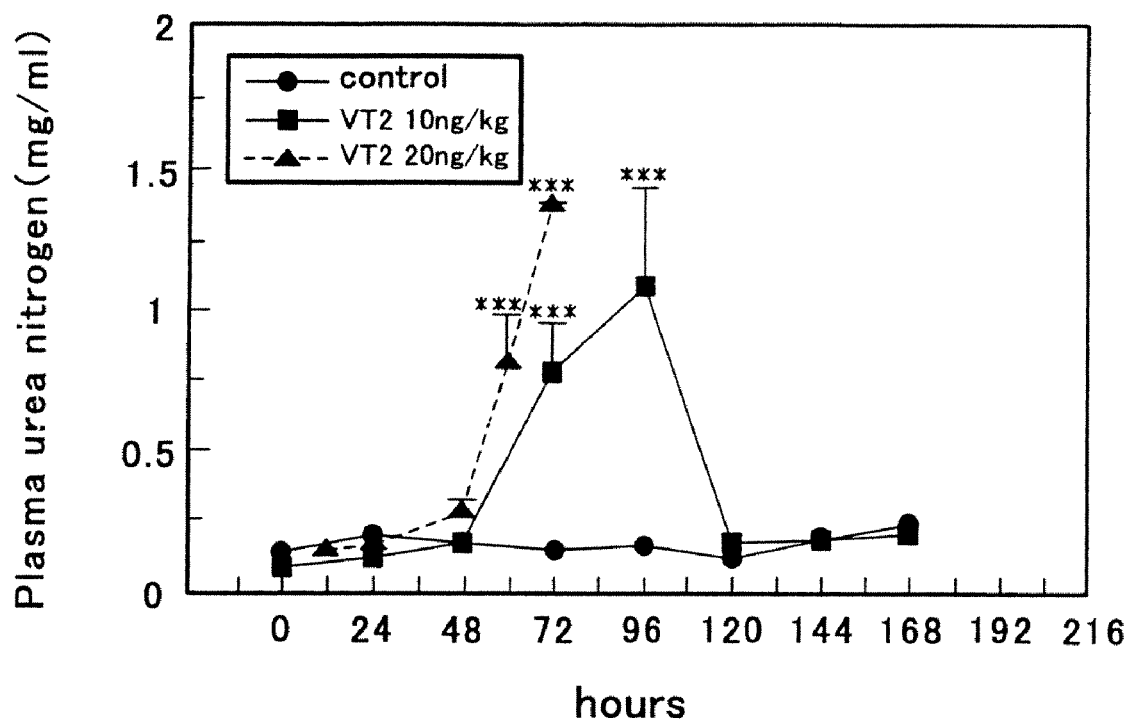
FIG. 6 is a graph showing time-dependent alteration of the amount of urea nitrogen contained in plasma for the verification of renal disorder caused by the administration of VT2 to rats.
Figure 7:
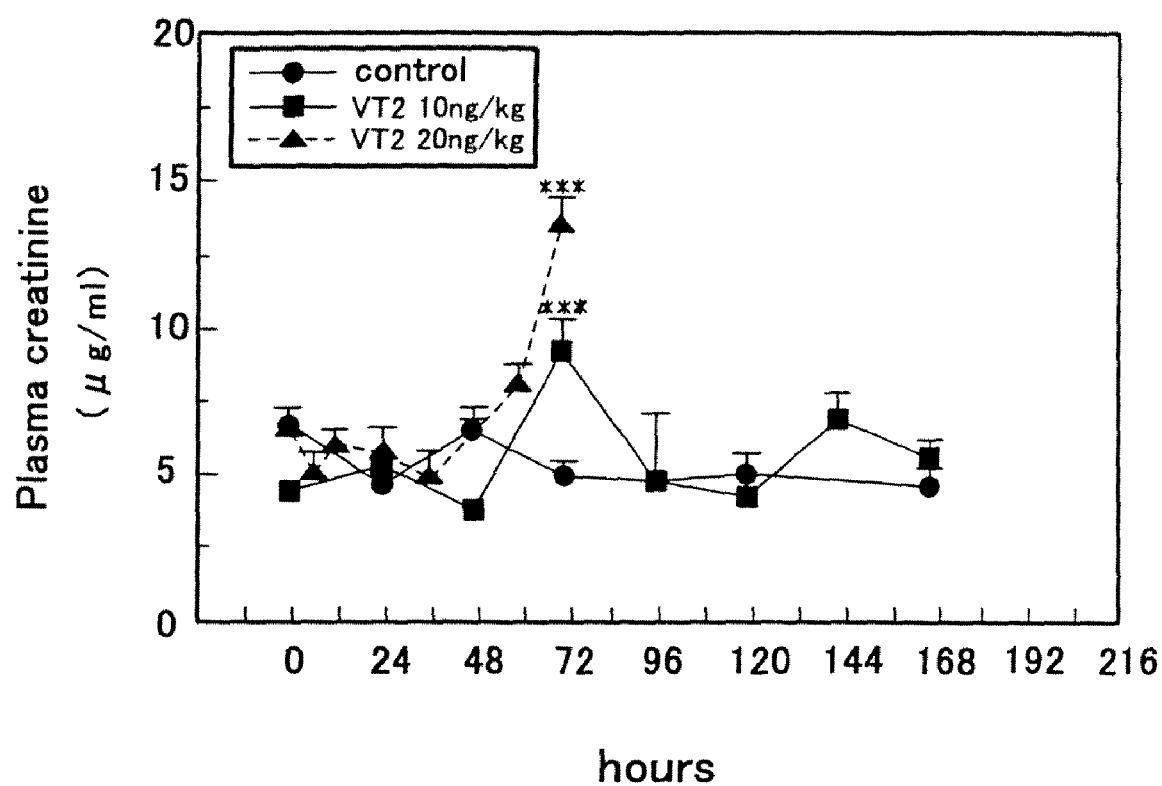
FIG. 7 is a graph showing time-dependent alteration of creatinine level in plasma for the verification of renal disorder caused by the administration of VT2 to rats.

Furthermore, in order to demonstrate influences on kidney glomerulus of rats treated with VT2 described in Example 5 above, urinary creatinine (FIG. 5), the amount of urea nitrogen in serum (BUN, FIG. 6) and serum creatinine (FIG. 7) were quantitatively determined. The amount of creatinine was determined using Creatinine-Test-Wako (alkaline picrate method, Wako Pure Chemical Industries, Ltd.). BUN was determined using Urea Nitrogen B-Test Wako (urease-indophenol method, Wako Pure Chemical Industries, Ltd.). In order to obtain serum, blood was collected from rat superior vena cava, thereto added with 7.6% sodium citrate solution at a ratio of 18:1, followed by the centrifugation at 2,000×g for 10 min to give a serum which was stored thereafter.

Consequently, it was found that the amount of urine and creatinine level decreased (FIG. 5), which were excreted within 24 hours just prior to the death, while the amount of urea nitrogen (FIG. 6) and creatinine level (FIG. 7) in plasma increased. Accordingly, the compromised function of glomerulus was observed in a final stage of disorder that was caused in VT2-treated rats

Example 10

Enhancement of the Amount of aquaporin 2 Excreted into Urine in Rats by an Intravenous Administration of VT2

The enhancement of the amount of the excreted urine accompanied by the lowered osmotic pressure illustrated in Examples 5 and 6 indicated the dysfunction involving a mechanism of water reabsorption (FIGS. 1 and 2). In order to demonstrate whether the failure in water balance by VT2 relates to the increase in the excretion of AQP2 into urine, an immunochemical measurement method (see, Example 2) was conducted in which an anti-AQP2 polyclonal antibody was used, which was produced using a C-terminal peptide of a rat water channel (AQP2) (see, Example 1).

Figure 8:
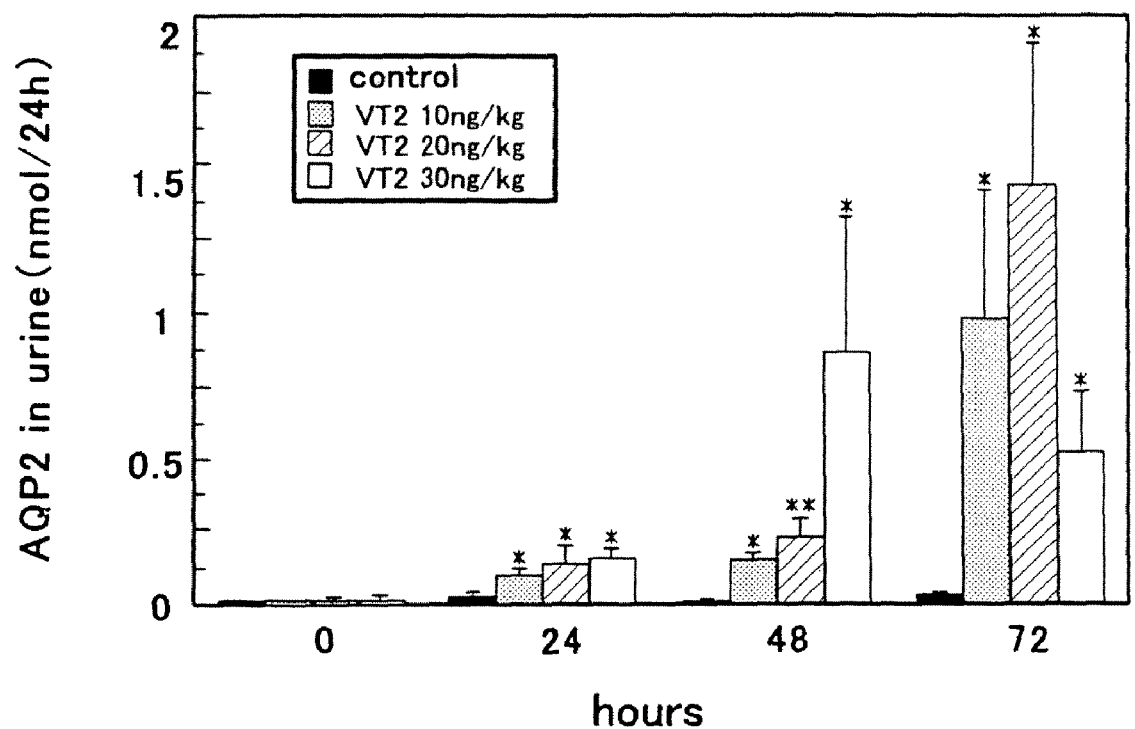
FIG. 8 is a graph showing time-dependent alteration of the amount of excretion of AQP2 into urine accompanied by the administration of VT2 to rats.

In accordance with this measurement method, AQP2 could be detected in the range of from 0 to 4,000 fmol of AQP2. The amount of AQP2 protein in urine from VT2-untreated rats was 13.0 pmol/mL (BCA Protein analytical reagent, employed standard value of protein was determined by Pierce Co., Ltd.). The concentration of AQP2 in the cumulative urine over 24 hours of VT2-treated rats significantly increased. The concentration of AQP2 in cumulative urine over 24 hours on day 2 significantly increased in rats administered with 10, or 30 ng/kg of VT2 in comparison with that of control rats (FIG. 8).

Therefore, it was indicated that the hemolytic uremic syndrome caused by VT2 was responsible for the rapid increase of the amount of AQP2 excreted into urine. Moreover, it was also revealed that correlation existed between the deteriorated renal function shown in Examples 5 to 9 and the amount of AQP2 excreted into urine.

Example 11

Study on AQP2 Expression in Renal Cell Membrane of VT2-Treated and Untreated Rats In accordance with the process in Example 4, the expression level of AQP2 in renal cell membrane of VT2-treated rats and untreated rats was examined by a western blotting method. Rats administered with VT2 were employed, which were treated by a process described above in Example 2.

Figure 9:
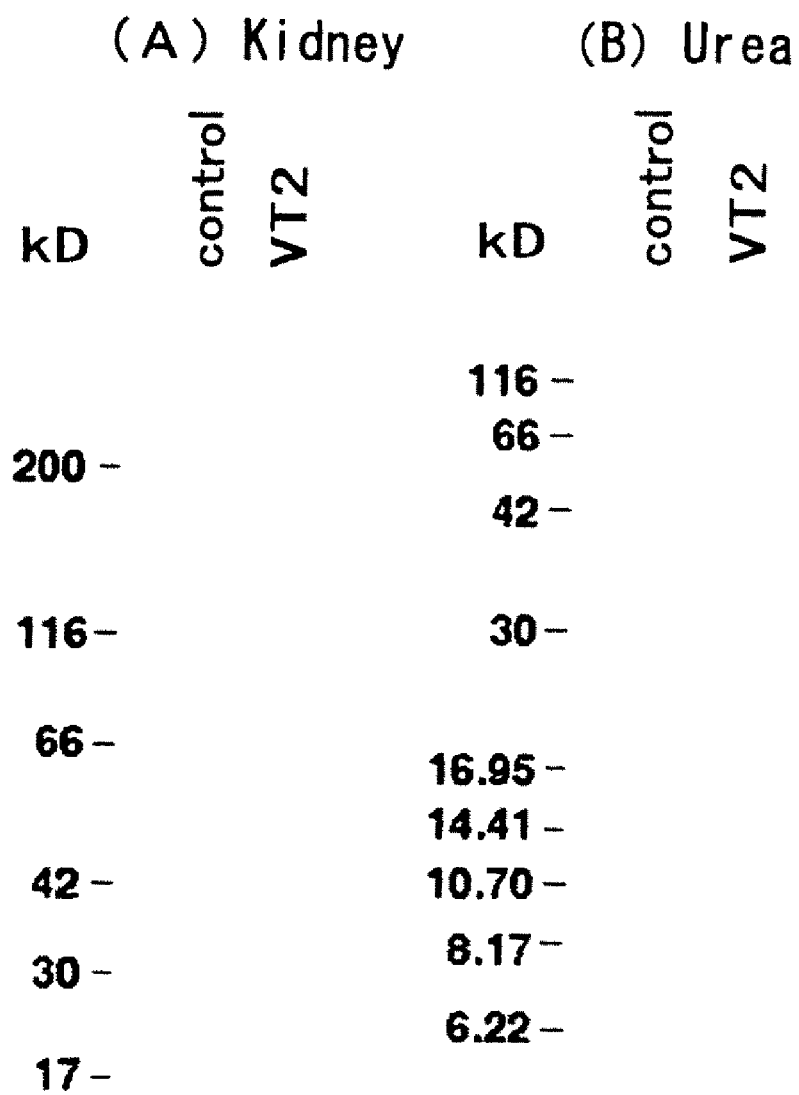
FIG. 9 is a drawing showing results of western blotting to examine changes of AQP2 in renal cell membrane and in urine accompanied by the administration of VT2 to rats.

Consequently as shown in FIG. 9, the enhanced excretion of AQP2 into urine through the administration of VT2 (FIG. 9 (B)) correlated to the lowered expression level of AQP2 in renal cell membrane (FIG. 9 (A)). Moreover, a wide band corresponding to a macromolecule of approximately 45 kDa that represents a molecular form into which a carbohydrate chain was introduced, and a band corresponding to AQP2 of 29 kDa were detected. The immunoreactivity of AQP2 protein (45 kDa) was found to be notably decreased in rats on 5 days after the administration of VT2. The urinary sample was centrifuged at 2,000×g, and a supernatant fraction therefrom was separated on SDS-PAGE, which was immunostained. Thus, no reactive band could be detected in VT2-untreated rats, while three positive bands that were reactive to the antibody of 7.5 kDa.14.4 kDa.45 kDa were detected in urine of rats on day 5 after the administration of VT2. In supernatants, which were obtained from the centrifugation at 2,000×g of urine that was occasionally collected and urine that was collected from bladder via a catheter, a majority part of AQP2 antibody-positive substances could be detected. Consequently, it was suggested that AQP2 that was detected in urine did not derive from cell-bound AQP2 but derived from the released AQP2 or the metabolite thereof from renal cells.

Example 12

Measurement of AQP2 Content in Urine from Human HUS Patient Developed by Infection in Gastrointestinal System by Pathogenic *E. Coli* O157:H7

Taking into account of the existence in human urine of substances that nonspecifically cross-react with anti-human AQP2 polyclonal antibody which was obtained by immunization and preparation using a C-terminal peptide of AQP2 that was derived from human followed by the purification on an affinity column, a highly sensitive immunochemical method for measuring human AQP2 was developed with higher specificity for the purpose of measuring the AQP2 level in human urine. That is, AQP2 in human urine was detected at high sensitivity by using the sandwich ELISA technique illustrated in Example 3.

Examination involving the highly sensitive measurement method of human AQP2 described above was conducted as shown in Table 2 for a patient (a girl of 3 years old) having HUS developed due to infection via a gastrointestinal system by pathogenic *E. coli* O157:H7, although antibiotics was administered prior to the onset of manifestation of diarrhea to prevent the bacterial colony formation. This patient developed abdominal pain, melena and oliguria on day 3 after the onset of the disease. At this time point, an urinary sample collected from the patient via a catheter was subjected to a quantitative determination, which consequently showed remarkable elevation of AQP2 level similarly to the level of $\beta$2-microglobulin. This patient received a continuous therapy by peritoneum dialysis, leading to the amelioration of HUS accompanied by decrease in the excretion of total protein into urine, and diminished serum creatinine level as well as urea nitrogen level. Furthermore, although the level of excretion of $\beta$2-microglobulin and N-acetyl-$\beta$-D-glucosamidase (NAG) into urine kept still high, AQP2 level in urine dropped.

Urinary osmotic pressure, $\beta$2-microglobulin in urine, NAG in urine, creatinine in serum and BUN in blood shown in Table 2 were measured in accordance with the methods described in Examples 6 to 9, and urinary protein was determined using BCA protein assay reagent (Pierce). For statistical analysis, ANOVA or independent t-test were employed.

TABLE 2

| Days post development (day) | Urine | | | | | serum | | |
|---|---|---|---|---|---|---|---|---|
| | Osmotic pressure (mOsm/kg) | AQP2 (fmol/mg creatinine) | β2-micro-globulin- (μg/mg creatinine) | N-acetyl-β-D-glucosamin-idase (U/mg creatinine) | Protein (mg/dl) | Creatinine (mg/dl) | BUN (mg/dl) |
| 3 | 307 | 681 | 868 | 44.40 | 895 | 5.4 | 147 |
| 14 | 242 | 0 | 1457 | 45.80 | 360 | 3.1 | 65 |

As a result, a relationship between the severity for morbidity of HUS in human and the amount of AQP2 excreted into urine was indicated. The severity for morbidity of HUS was, in other words, envisaged to correlate to renal disorder as well as the severity of enterohemorrhagic E. coli infection. Accordingly, it was suggested that the determination of the amount of AQP2 excreted into urine was applicable to a quick diagnosis of morbidity of HUS as well as a diagnosis of severity of these diseases.

Example 13

Enhancement of the Amount of Excretion of AQP2 into Rat Urine by an Intravenous Administration of VT1

In a similar manner as described above in Example 2, male Wistar rats of 4 weeks old were intravenously administered with 10, 40 and 100 ng/kg·weight of VT1 dissolved in 100 μl of saline containing rat serum albumin (Sigma, St Louis, Mo.). Thereafter, time-dependent alteration of the amount of rat water channel (AQP2) excreted into urine was measured in a similar manner as in Example 1 by an immunochemical measurement process (see, Example 2) in which an anti-AQP2 polyclonal antibody (see, Example 1) was utilized, which was prepared using a C-terminal peptide of AQP2 similarly to that described in Example 1. VT1 employed in this experiment was purified from a culture supernatant of E. coli O157.H7 according to the procedure in Noda, M. et. al., Microb. Pathogenesis, 2: 339-349, 1987.

Figure 10:
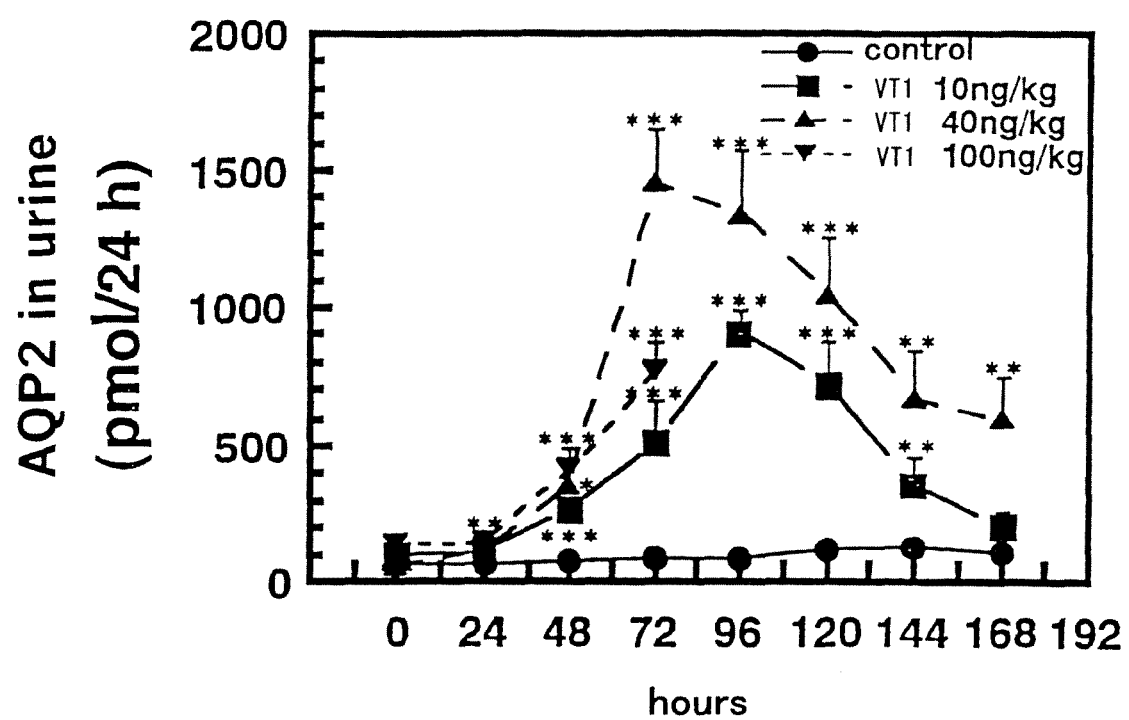
FIG. 10 is a graph showing time-dependent alteration of the amount of excretion of AQP2 into urine accompanied by the administration of VT1 to rats.

The results are shown in FIG. 10, which reveal that the concentration of AQP2 in urine was significantly elevated, starting from 48 hours after the administration of VT1 at 10 ng/kg and 40 ng/kg, and starting from 24 hours after the administration of VT1 at 100 ng/kg. These results reveal that AQP2 was also excreted into urine upon the exposure to VT1, and thus, the measurement of the concentration of AQP2 in urine could be utilized for a quick diagnosis of infectious disease resulting from enterohemorrhagic E. coli that produce VT1.

Example 14

Enhancement of the Amount of Excretion of AQP2 into Rat Urine by an Intravenous Administration of VT1 or VT2

Figure 11:
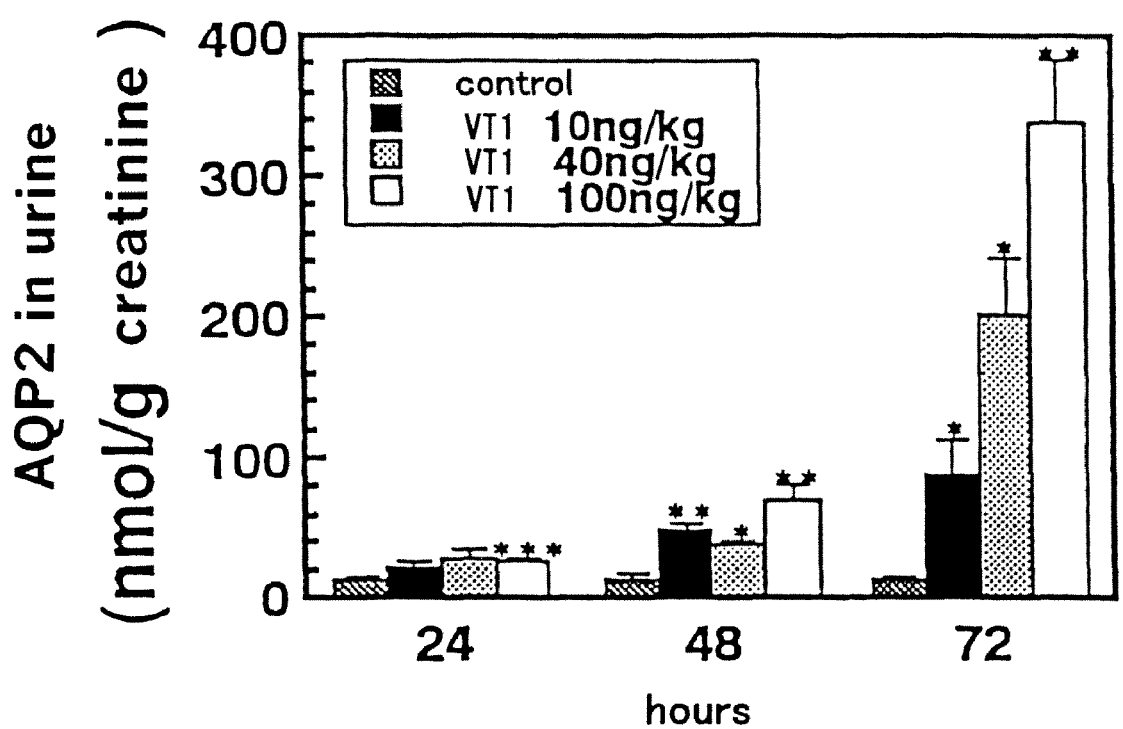
FIG. 11 is a graph showing time-dependent alteration of the amount of excretion of AQP2 into urine accompanied by the administration of VT1 to rats.
Figure 12:
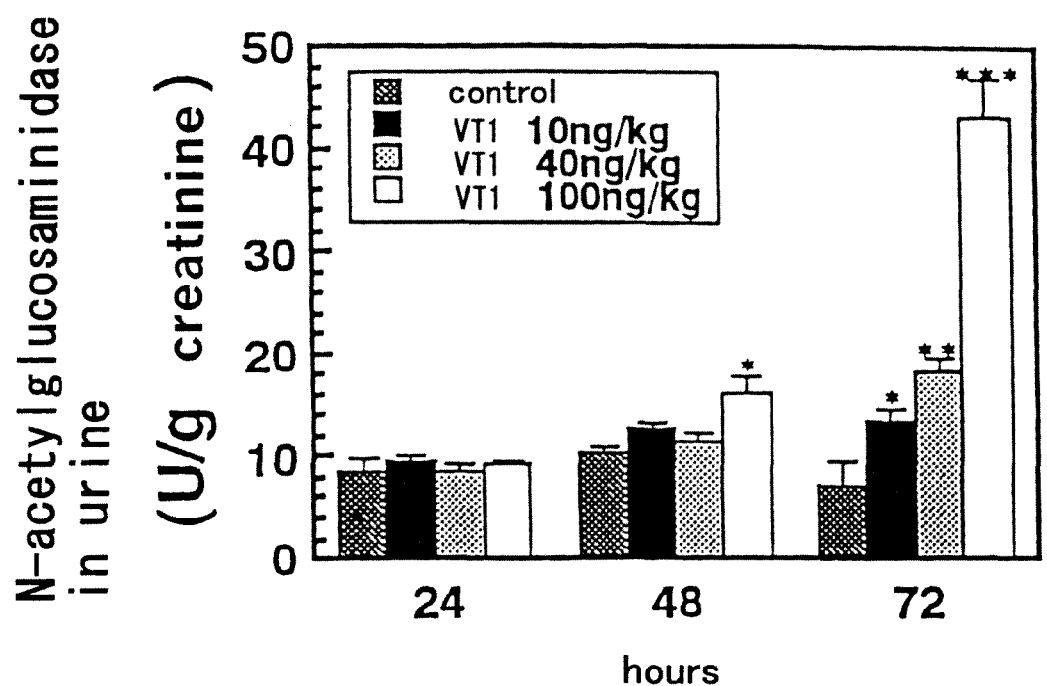
FIG. 12 is a graph showing time-dependent alteration of the amount of excretion of NAG into urine for the verification of renal disorder caused by the administration of VT1 to rats.
Figure 13:
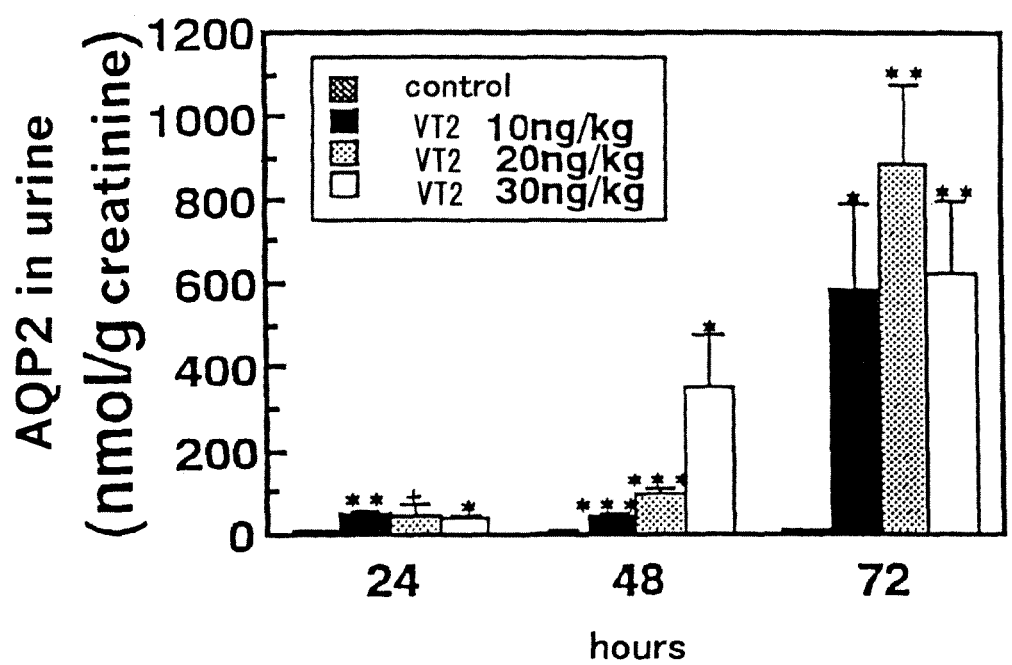
FIG. 13 is a graph showing time-dependent alteration of the amount of excretion of AQP2 into urine accompanied by the administration of VT2 to rats.
Figure 14:
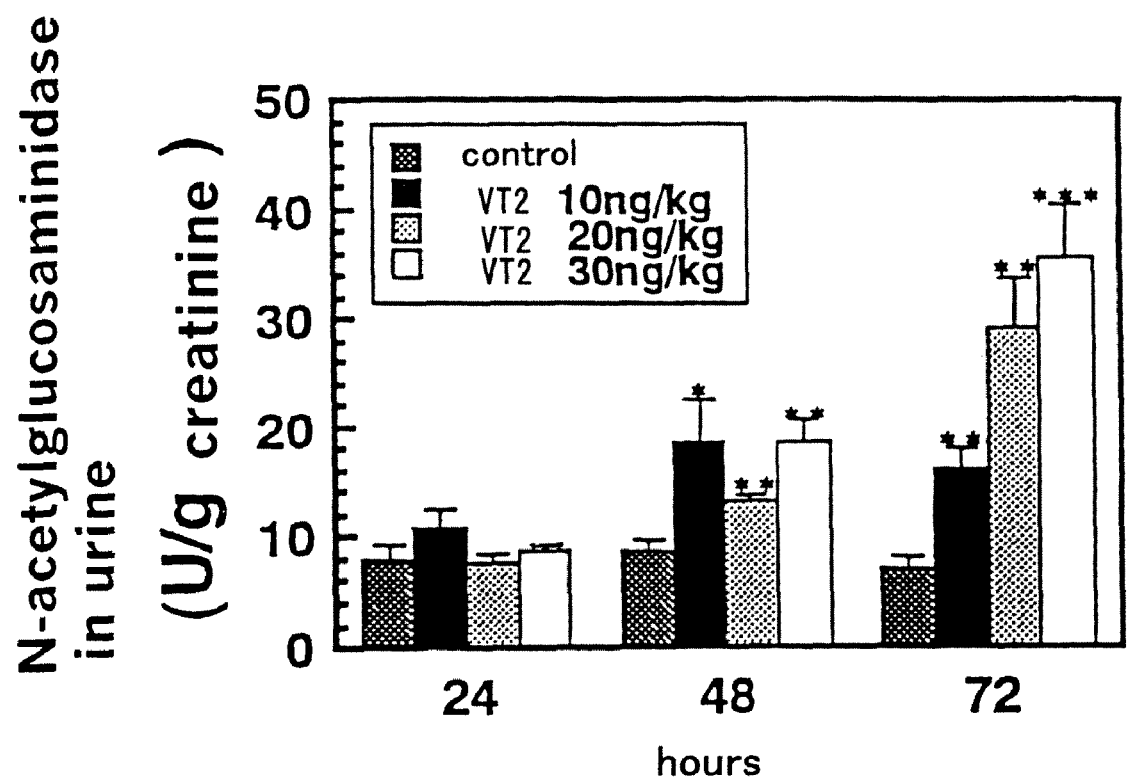
FIG. 14 is a graph showing time-dependent alteration of the amount of excretion of NAG into urine for the verification of renal disorder caused by the administration of VT2 to rats.

In similar manners as described above in Examples 13 and 2 respectively, VT1 or VT2 was administered to rats, and thereafter, the amount of NAG (see, Example 8) and creatinine (see, Example 9) excreted into urine was measured with time dependent in addition to the concentration of AQP2 in urine. Thus obtained results are shown as AQP2 concentration (FIGS. 11 and 13) and NAG concentration (FIGS. 12 and 14) of post correction with creatinine. As shown in FIG. 11, the amount of AQP2 excreted into urine was found to increase in a dose dependent manner by the administration with VT1, with a significant difference from the control at 24 hours after the administration at a dose of 100 ng/kg. Furthermore, as shown in FIG. 13, the amount of AQP2 excreted into urine increased in a dose dependent manner upon the administration of VT2, with a significant difference from the control at 24 hours after the administration at a dose of 10 ng/kg or more. Moreover, as shown in FIGS. 12 and 14, the amount of N-acetyl-β-D-glucosaminidase excreted into urine also increased in a dose dependent manner through the administration of VT1 and VT2, however, the significant difference from the control was observed after 48 hours or later in any of these. Accordingly, it was indicated that the amount of excretion of AQP2 increased at an earlier stage.

From the results hereinabove, it was revealed that the amount of AQP2 in urine was useful as an indicator for the exposure to VT1 and VT2, and thus, the measurement of the concentration of AQP2 in urine was suggested to be utilizable for quick diagnoses of infectious diseases by enterohemorrhagic E. coli that may produce VT1 and/or VT2.

INDUSTRIAL APPLICABILITY

In accordance with Examples disclosed hereinabove, it was clearly indicated that several kinds of renal disorders, in particular, renal disorder caused by infection from enterohemorrhagic E. coli, could be quickly found by using AQP2 as an indicator, based on the observation that significant increase of excretion of AQP2 into urine was found earlier than known indicators for renal disorders, i.e., β2-microglobulin and N-acetyl-β-D-glucosaminidase. In addition, infection by enterohemorrhagic E. coli can be diagnosed at an early stage by using AQP2 as an indicator. Moreover, because positive correlationships between the amount of AQP2 excreted, and the amount of exposure to VT1 or VT2, the extent of renal disorder, systemic symptoms were respectively shown, the degree of risk for transition to HUS, renal disorders and the like can be indirectly diagnosed by using AQP2 as an indicator in accordance with the present invention.

We claim:

1. A method for diagnosing enterohemorrhagic *E. coli* infection comprising: detecting the excretion of aquaporin 2 into urine or determining the amount of the excretion of the same into urine of a subject; and diagnosing enterohemorrhagic *E. coli* infection in said subject.

2. The method according to claim 1, wherein said enterohemorrhagic *E. coli* infection results in a renal disorder.

3. The method according to claim 1, wherein said enterohemorrhagic *E. coli* infection results in hemolytic uremic syndrome.

4. The method according to claim 1, wherein the *E. coli* is a verotoxin-producing strain.

5. The method according to claim 4, wherein the verotoxin-producing strain is a verotoxin 2-producing strain.

6. The method according to claim 4, wherein the verotoxin-producing strain is O-157:H7.

7. The method according to claim 4, wherein the verotoxin-producing strain is a verotoxin 1-producing strain.

8. The method according to claim 1, wherein the detection or quantitative determination of the aquaporin 2 is conducted by an immunoassay.

9. The method according to claim 8, wherein the immunoassay is an ELISA technique.

* * * * *